United States Patent
Young et al.

(10) Patent No.: US 7,598,072 B2
(45) Date of Patent: Oct. 6, 2009

(54) ASSAY TO DETECT VIRAL UNCOATING

(75) Inventors: John A. T. Young, San Diego, CA (US); Shakti Narayan, Palo Alto, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 146 days.

(21) Appl. No.: 11/007,145

(22) Filed: Dec. 8, 2004

(65) Prior Publication Data

US 2006/0099606 A1    May 11, 2006

Related U.S. Application Data

(60) Provisional application No. 60/528,253, filed on Dec. 9, 2003.

(51) Int. Cl.
*C12N 7/02* (2006.01)
*A61K 39/12* (2006.01)
(52) U.S. Cl. .................................. 435/239; 424/204.1
(58) Field of Classification Search .................. None
See application file for complete search history.

(56) References Cited

OTHER PUBLICATIONS

Narayan et al. Journal of Virology, Feb. 2003, 77(3):1977-1983.*
Barnard, R. J., et al., "Low pH is required for avian sarcoma and leukosis virus Env-dependent viral penetration into the cytosol and not for viral uncoating.", *J Virol.*, 78(19), (Oct. 2004),10433-41.
Melikyan, G. B., et al., "Low pH is required for avian sarcoma and leukosis virus Env-induced hemifusion and fusion pore formation but not for pore growth.", *J Virol.*, 78(7), (Apr. 2004),3753-62.

* cited by examiner

*Primary Examiner*—Stacy B Chen
(74) *Attorney, Agent, or Firm*—Schwegman, Lundberg & Woessner, P.A.

(57) ABSTRACT

A cell-free viral uncoating assay is provided.

16 Claims, 18 Drawing Sheets

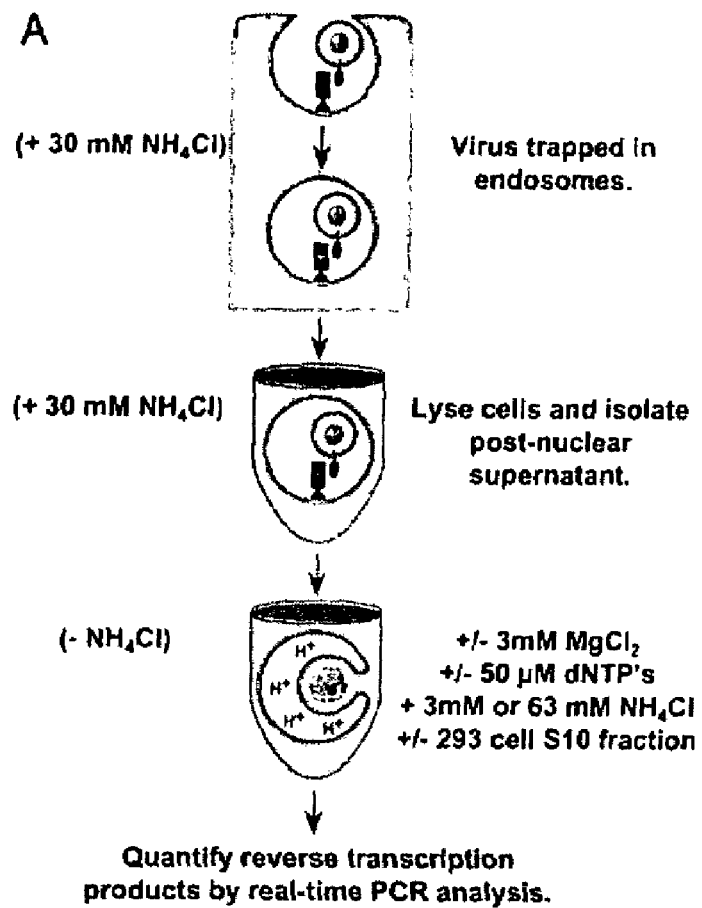
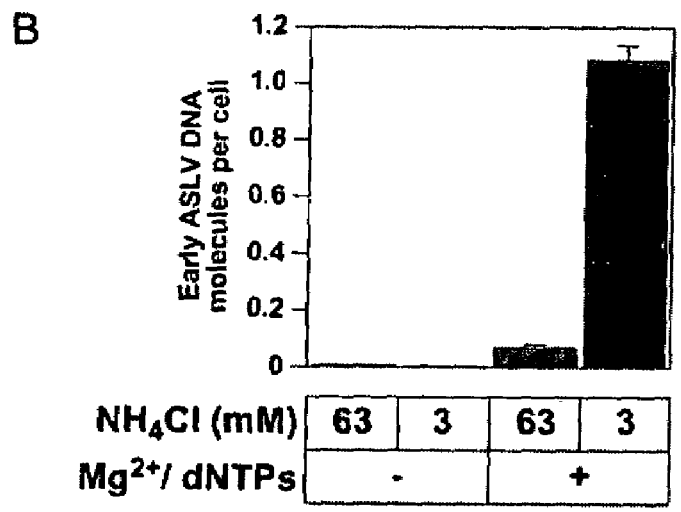
Fig 16

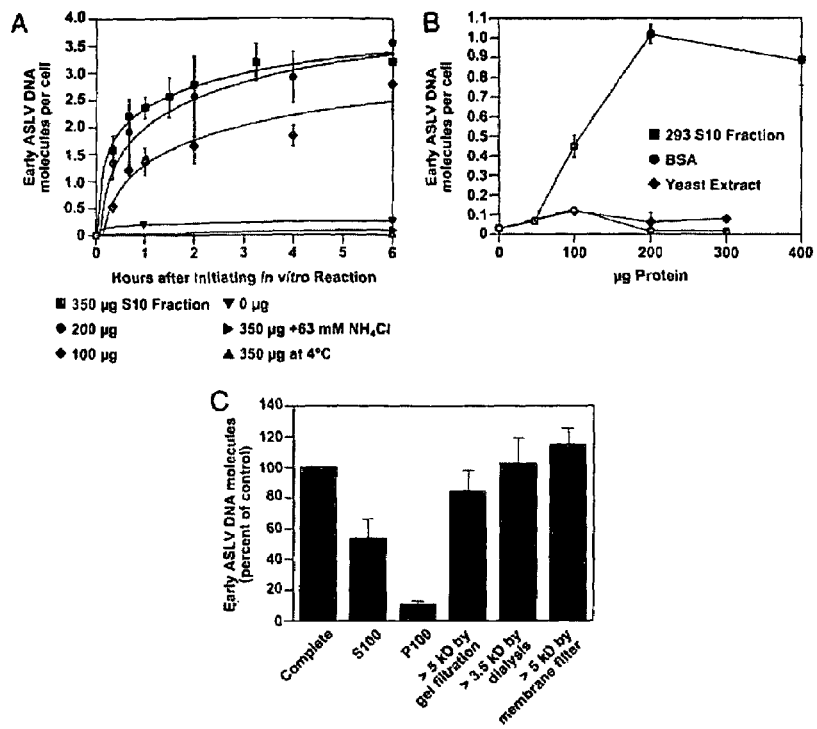
Fig 17
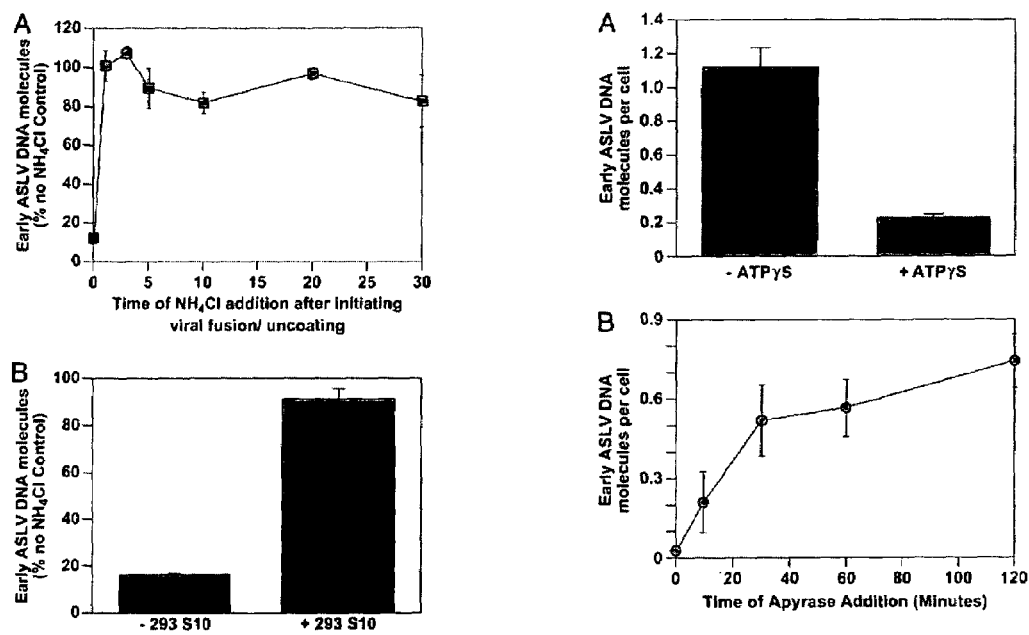
Fig 18
Fig 19

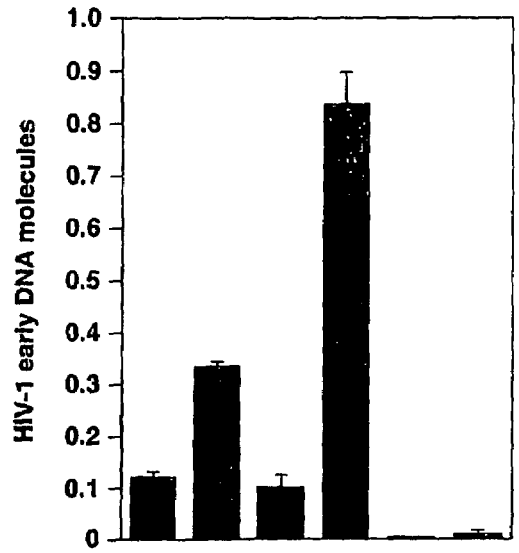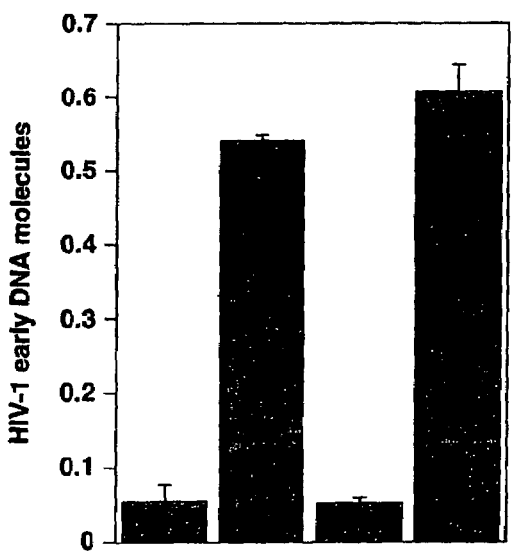
Fig 21

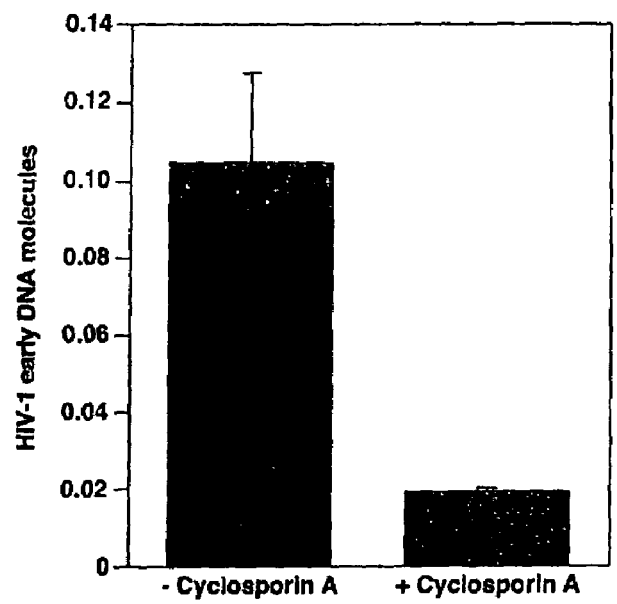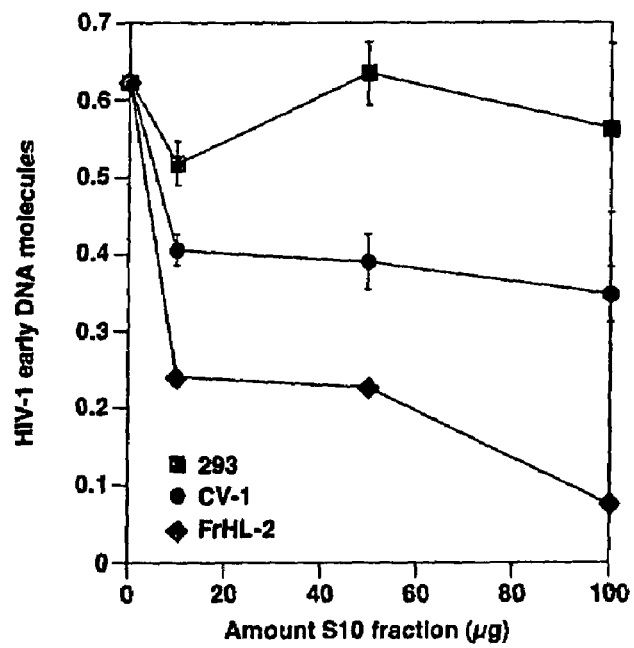
Fig 22

ASSAY TO DETECT VIRAL UNCOATING

CROSS-REFERENCE TO RELATED APPLICATIONS

This application claims the benefit of the filing date of U.S. application Ser. No. 60/528,253, filed Dec. 9, 2003, under 35 U.S.C. § 119(e), the disclosure of which is incorporated by reference herein.

STATEMENT OF GOVERNMENT RIGHTS

The present invention was made, at least in part, with a grant from the Government of the United States of America (grant CA070810 from the National Institutes of Health). The Government may have certain rights to the invention.

BACKGROUND

To initiate infection, the lipid bilayer of an enveloped virus must fuse with a cellular membrane for delivery of the viral nucleocapsid to the host cell cytoplasm. These events involve conversion of the viral envelope glycoprotein (Env) from its native, metastable state to its fusion-activated form, which represents its lowest energy state (Eckert et al., 2001). Viral envelope glycoproteins are triggered to activate fusion either by pH-independent or pH-dependent mechanisms. Following virus uptake, low-pH-dependent viral glycoproteins are triggered by the acidic environment of an endosomal compartment. In contrast, pH-independent viral glycoproteins seem to be activated as a consequence solely of receptor interaction (Eckert et al., 2001; Hernandez et al., 1996).

Recent data obtained with the avian sarcoma and leukosis virus (ASLV) system have provided evidence for a third type of triggering mechanism in which receptor interaction converts (primes) the viral envelope protein so that it becomes sensitive to low-pH-induced activation (Mothes et al., 2000). In support of this two-step model, ASLV entry is blocked by lysosomotropic agents that act to neutralize the low pH of endosomal compartments (Lamaze et al., 2001; Mothes et al., 2000). Also, ASLV Env-dependent cell-cell fusion leading to syncytium formation requires both receptor contact and a low-pH-induced activation signal. Moreover, low pH treatment abolishes the infectivity of soluble receptor-bound virions, generating thermostable sodium dodecyl sulfate (SDS)-resistant oligomers of the viral transmembrane subunit of Env, a property consistent with fusion activation (Mothes et al., 2000).

What is needed is an assay to detect viral entry pathways.

SUMMARY OF THE INVENTION

The invention provides an uncoating assay that is based upon the interaction between a viral membrane bound protein (e.g., Env) and a cellular receptor, which interaction under certain conditions allows for viral accumulation in endosomes. In one embodiment, the viral membrane bound protein is subgroup A ASLV Env. In one embodiment, the cellular receptor is the TVA receptor. In one embodiment, the receptor is a GPI anchored receptor, e.g., a GPI anchored TVA receptor. In one embodiment, the viruses which accumulate in the endosome are pseudotyped viruses. A pseudotyped virus is an infectious virus where the viral membrane bound protein which binds a cellular receptor is heterologous to one or more structural and/or catalytic viral proteins in the virion. Such an assay may be employed to screen for drugs that block uncoating of HIV-1 and other enveloped viruses, to identify the target for ATP-gammaS which blocks retroviral uncoating, to define the molecular mechanisms of cyclophilin A action and cyclosporin A inhibition of HIV-1 DNA synthesis, to define the molecular mechanism of Lv-1 restriction, or to screen for viral inhibitors, e.g., to screen for inhibitors of viruses in one or more of the following families: Rhabdoviridae (e.g., rabies virus and VSV), Orthomyxoviridae (e.g., influenza A viruses), Paramyxoviridae (e.g., Sendai virus, human and bovine parainfluenza viruses, measles virus, human and bovine respiratory syncytial viruses (RSV), and Mumps virus), Retroviridae (including HIV-1, HIV-2, SIV, HTLV-1, HTLV-2), Bunyaviridae (including Hantavirus), Arenaviridae (including Lassa fever virus, and Argentine and Venezeulan hemorrhagic fever viruses), Hepadnaviridae (including Hepatitis B virus), Togaviridae (including Rubella virus and the alphaviruses Sindbis, Ross River, and Semliki Forest viruses, Eastern equine encephalitis virus, Western equine encephalitis virus, and Venezuelan equine encephalitis virus), Flaviviridae (including hepatitis C viruses, tick-borne encephalitis virus, Dengue virus, West nile fever virus, St Louis encephalitis virus, yellow fever virus, Kyasanur forest disease virus, Omsk hemorrhagic Fever virus), Coronaviridae (including the SARS virus), Arteriviruses, or Filoviridae (including Marburg and Ebola viruses).

As described herein, a cell-free system that recapitulates early steps of retroviral replication was developed by using avian sarcoma and leukosis virus as a model retrovirus. The substrates used in this system were viral particles that were trapped before completing membrane fusion. These virions are induced to fuse out of endosomes and the viral cores are released into solution where they are amenable to biochemical manipulation. This system revealed that membrane fusion is not sufficient to stimulate the formation of a reverse transcription complex. Instead, ATP hydrolysis and cellular factors >5 kDa in size were required. Furthermore, later steps of reverse transcription were stimulated by nuclear factors. The cell-free system thus allows for characterization of retroviral uncoating mechanisms and facilitates the identification and characterization of cellular factors involved in post-fusion steps in viral infection.

The invention thus provides a cell-free method for release of enveloped viruses from endosomes. The method includes providing a cell-free sample comprising intact endosomes comprising fusion arrested enveloped viral particles (isolated, virus containing endosomes). As used herein, "isolated" refers to in vitro preparation, isolation and/or purification of a nucleic acid, protein, peptide, virus, subcellular structure, e.g., endosomes, so that they are not associated with substances they are associated with in nature or substantially free from at least one contaminating substance they are normally associated with in vivo. Thus, for example, an isolated substance may be prepared by using a purification technique to enrich it from a source mixture. The endosomes are isolated from cells that express one or more viral receptors and are infected with an enveloped virus having a membrane bound protein which binds at least one of the viral receptors. The sample is then subjected to conditions that allow for virus particle-endosomal membrane fusion and release of viral cores from endosomes.

In another embodiment, the invention provides a cell-free method to detect or determine post viral envelope-endosome fusion events. The method includes subjecting a cell-free sample comprising intact endosomes comprising fusion arrested enveloped viral particles to conditions that allow for virus particle-endosomal membrane fusion and release of viral cores from endosomes yielding a composition comprising viral cores. The endosomes are isolated from cells that express one or more viral receptors and are infected with an enveloped virus having a membrane bound protein which binds at least one of the viral receptors. Then viral uncoating or viral nucleic acid replication is detected or determined. In one embodiment, the composition is subjected to conditions that allow for or enhance viral uncoating or viral replication such as the addition of one or more reagents, e.g., one or more cellular factors, e.g., isolated cellular factors, or subcellular fractions, e.g., a S10 fraction, one or more nucleotides and/or one or more salts, e.g., $MgCl_2$ or $MnCl_2$, and temperatures above 0 degrees.

The invention also provides a method to detect or determine a modulator of viral uncoating. The method includes providing endosomes isolated from cells expressing a viral receptor and contacted with a virus, e.g., a recombinant virus, comprising a membrane bound protein which binds to the receptor and one or more agents under conditions which are permissive for viral binding to the receptor and endocytosis, but not release from endosomes. Conditions are then altered to allow for release from endosomes. In one embodiment, the conditions alter endosomal pH, for instance, by using lysosomotropic agents, e.g., bafilomycin A1. It is then determined whether the one or more agents modulate, i.e., increase or decrease, post-fusion events such as viral uncoating. In one embodiment, the agent is a cellular factor. In one embodiment, the one or more agents inhibit or block uncoating of viruses in one or more of the following families: Rhabdoviridae, Orthomyxoviridae, Paramyxoviridae, Retroviridae, Bunyaviridae, Arenaviridae, Hepadnaviridae, Togaviridae, Flaviviridae, Coronaviridae, Arteriviruses, or Filoviridae. In one embodiment, the virus is a pseudotyped rhabdovirus, orthomyxovirus, paramyxovirus, retrovirus, lentivirus, bunyavirus, arenavirus, hepadnavirus, flavivirus, coronavirus, or filovirus. The viral core for the pseudotype may be a core from any virus including but not limited to rhabdovirus, orthomyxovirus, paramyxovirus, retrovirus, lentivirus, bunyavirus, arenavirus, hepadnavirus, flavivirus, coronavirus, or filovirus, and the membrane bound protein is subgroup A ASLV Env. In one embodiment, the cells are recombinant cells, for instance, those expressing a recombinant viral receptor. In one embodiment, the cells are contacted with the one or more agents after or before the cells are contacted with the virus, e.g., recombinant virus.

Also provided is a method in which endosomes isolated from cells expressing a viral receptor and contacted with a virus, such as a recombinant virus, comprising a membrane bound protein which binds to the receptor under conditions which are permissive for viral binding to the receptor and endocytosis but not release from endosomes, are contacted with one or more agents and conditions are altered to provide for release of virus from endosomes via membrane fusion. It is then detected or determined whether the one or more agents modulate post-fusion events including viral uncoating. In one embodiment, the recombinant virus is a pseudotyped virus, e.g., a virus with a HIV core and ASLV Env. In one embodiment, the virus is a pseudotyped rhabdovirus, orthomyxovirus, paramyxovirus, retrovirus, lentivirus, bunyavirus, arenavirus, hepadnavirus, flavivirus, coronavirus, or filovirus. The viral core for the pseudotype may be a core from any virus including but not limited to rhabdovirus, orthomyxovirus, paramyxovirus, retrovirus, lentivirus, bunyavirus, arenavirus, hepadnavirus, flavivirus, coronavirus, or filovirus, and the membrane bound protein is subgroup A ASLV Env. In one embodiment, the cells are recombinant cells, for instance, those expressing a recombinant viral receptor. In one embodiment, the viral receptor is TVA. In one embodiment, the agent is a cellular factor. In one embodiment, the one or more agents inhibit or block uncoating of viruses in one or more of the following families: Rhabdoviridae, Orthomyxoviridae, Paramyxoviridae, Retroviridae, Bunyaviridae, Arenaviridae, Hepadnaviridae, Togaviridae, Flaviviridae, Coronaviridae, Arteriviruses, or Filoviridae. In one embodiment, the cells are contacted with the one or more agents after or before the cells are contacted with the virus, e.g., recombinant virus.

Also provided a preparation of isolated intact, virus containing endosomes, e.g., wherein the virus is pseudotyped virus. In one embodiment, the preparation is obtained by infecting cells comprising a cellular receptor for a virus with the virus under conditions that permit endocytosis of the virus to endosomes but not release from endosomes, lysing infected cells, and isolating endosomes from the cell lysate.

BRIEF DESCRIPTION OF THE DRAWINGS

FIG. 5. Mechanisms of activating viral membrane fusion. Viral envelope proteins require activation prior to mediating membrane fusion. The envelope proteins of pH-independent viruses are activated by interactions with the cellular receptor, and in some cases by additional interactions with co-receptors. Thus, most pH-independent viruses are thought to fuse at the cell surface. For pH-dependent viruses, activation occurs by exposure of the viral envelope proteins to the low pH environment of acidic intracellular organelles following receptor-mediated endocytosis. In this case, one function of the cellular receptor is to allow virus attachment to the cell surface prior to endocytosis. While pH-dependent and pH-independent envelope proteins differ in their signals for activating fusion, the basic mechanisms of the fusion reactions mediated by these proteins are likely very similar.

Fractions of each gradient were subjected to electrophoresis on a 12% polyacrylamide gel containing SDS followed by immunoblotting with an antibody specific for DsRed (Kaykas et al., 2001) (A and B) or with a subgroup A SU-immunoglobulin fusion protein (Zingler et al., 1996) to detect TVA800 (C and D) or TVA950 (E). The relative levels of TVA800 in different fractions of the sucrose gradients prepared with samples from untreated or MβCD-treated cells (F) were measured using quantitative immunoblotting. The figure shown is representative of such an experiment. The mean and standard deviations of TVA800 levels in both soluble and lipid raft fractions were calculated from three independent experiments.

Figure 12:
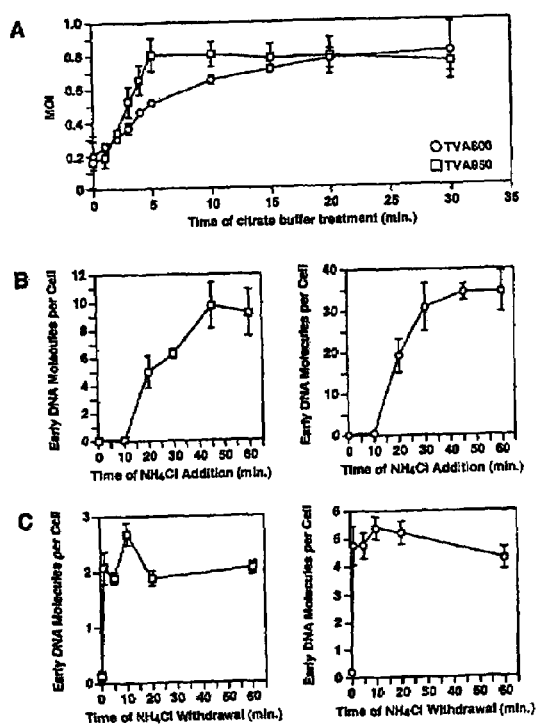

FIG. 12. Kinetics of viral uptake and trafficking via TVA950 and TVA800. An ASLV-A viral vector encoding EGFP [RCASBP(A)-EGFP] was bound on ice to transfected human 293 cells expressing either TVA950 (open squares) or TVA800 (open circles), and infection was then initiated by shifting the temperature to 37° C. (A) Internalization of ASLV-A virions from the cell surface via TVA800 and TVA950 occurs with different kinetics. At the different indicated time points after initiating infection, cells were treated with citrate buffer (pH 3.0) to inactivate surface-associated virions and infection of cells was subsequently determined by monitoring EGFP expression by flow cytometry. The MOI was calculated (in EGFP-transducing units) from the proportion of EGFP-positive cells (MOI=−ln [1−(percent EGFP-positive cells/100)], and the combined results of four independent experiments with standard deviations are shown. (B) ASLV-A virions entering cells via either TVA950 or TVA800 reach the putative acidic fusion compartment with similar kinetics. At the different times indicated after initiating infection, 30 mM $NH_4Cl$ was added for 10 hours and then the amount of early viral DNA products generated was determined by real-time QPCR. A standard curve for enumeration was generated by using a dilution series of known amounts of proviral RCASBP(A)-EGFP DNA in a plasmid vector. Shown are representative experiments carried out at an MOI of 0.8 (TVA950) or 2.8 (TVA800) EGFP-transducing units. No significant kinetic differences were observed if cells expressing TVA800 were infected instead at an MOI of 0.02 EGFP-transducing units (data not shown). Error bars represent the standard deviations of the data. (C) ASLV-A virions resume infection immediately upon removal of $NH_4Cl$. After blocking infection for 6 hours with 30 mM $NH_4Cl$, the inhibitor was washed out for the times indicated before the cells were placed again in medium containing the inhibitor for approximately 11 hours. The number of early reverse transcription products that had been generated in each cell population was then determined as described in the legend to panel B. A representative experiment of three independent experiments done in triplicate is shown. Error bars represent standard deviations of the data.

Figure 13:
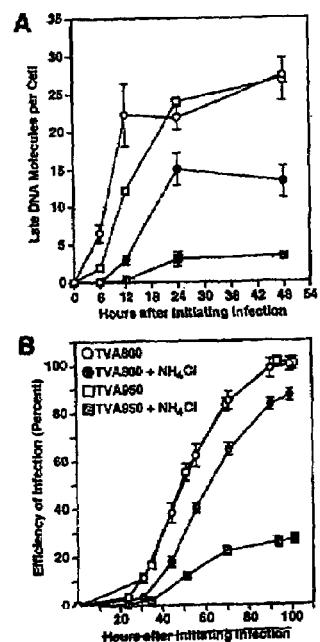

FIG. 13. $NH_4Cl$-arrested virions remain highly infectious when they use the TVA800 but not the TVA950 receptor. RCASBP(A)-EGFP was bound to transduced 293 cells expressing either TVA800 (circles) or TVA950 (squares), and infection was initiated either in the absence (open symbols) or presence (closed symbols) of a 6 hour block by 30 mM $NH_4Cl$ treatment. (A) At the indicated time points, the number of late reverse transcription products synthesized was determined as described in the legend to FIG. 12B. (B) A similar experiment was performed, but this time the number of resultant EGFP-positive cells was determined by flow cytometry at the indicated time points after initiating infection. These values were used to determine the efficiency of infection, defined as a percentage of that seen with untreated cells (MOI=1.5 EGFP-transducing units). Representative experiments of three independent experiments that were each performed in triplicate are shown. Error bars represent the standard deviations of the data.

Figure 14:
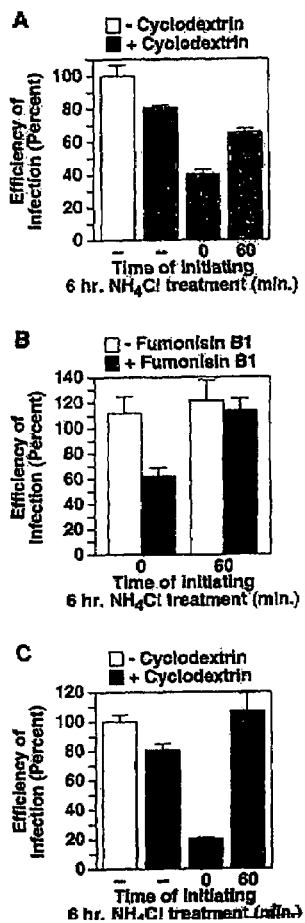

FIG. 14. Disruption of DRMs leads to a loss of infectivity of $NH_4Cl$-arrested virions in TVA800 expressing cells but not in cells expressing TVA950. To disrupt DRMs, human 293 cells expressing TVA800 (A) or TVA950 (C) were treated for 15 minutes with SFM containing 15 mM MβCD, 293 cells expressing TVA800 were treated with 40 µg of Fumonisin B1/ml for 60 hours (B), or the cells were left untreated before challenge with RCASBP(A)-EGFP. Where indicated, a 6 hour block to infection was imposed with 30 mM $NH_4Cl$ added just prior to (t=0) or 60 minutes after (t=60) initiating infection. The number of resultant EGFP-positive cells was determined by flow cytometry about 100 hours after initiating infection. The efficiency of infection is shown as a percentage of that level obtained with untreated cells (MOI=1.6 [A], 0.16 [B], and 1.4 [C] EGFP-transducing units). In each case, a representative experiment performed in triplicate is shown. Error bars represent the standard deviations of the data.

Figure 15:
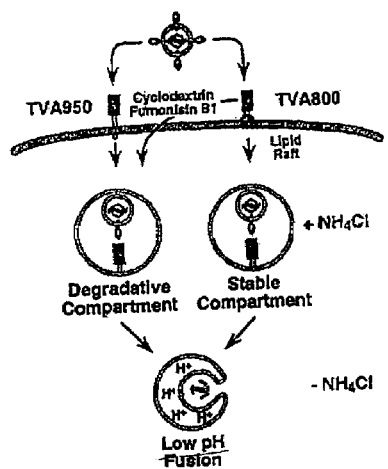
Figure 2D:
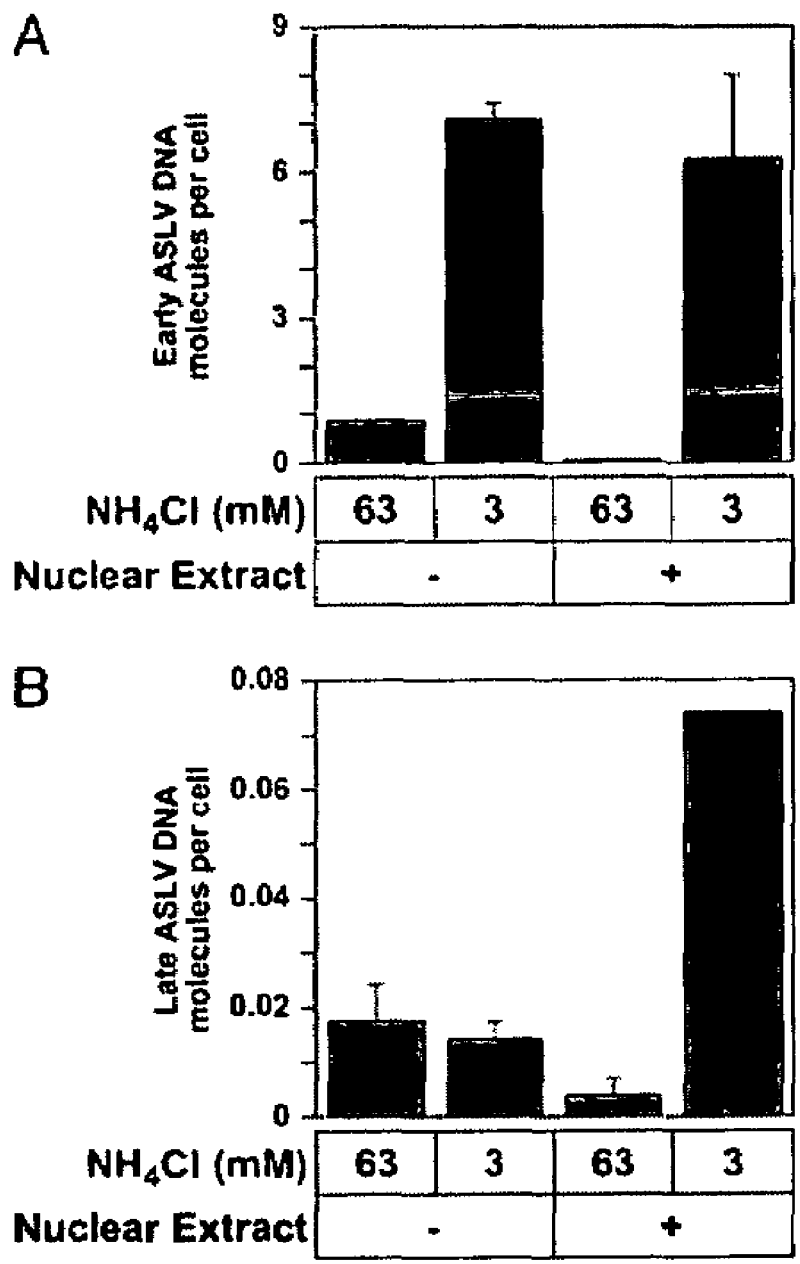

FIG. 15. Model for ASLV-A entry via transmembrane and GPI-anchored receptors. Virions bound to TVA950 are predicted to be taken up into cells by endocytosis and, in the presence of $NH_4Cl$, accumulate in a degradative compartment. In contrast, virions bound to TVA800 are predicted to utilize a lipid raft-dependent endocytic pathway and accumulate within a fusion compartment where they remain stable. Disruption of lipid rafts leads to viral accumulation in a degradative compartment instead. Infection resumes immediately after $NH_4Cl$ withdrawal, suggesting that virions may fuse directly with membranes of the endosomes in which they are trapped during inhibitor treatment.

FIG. 16. A cell-free system to study ASLV fusion and uncoating. (A) A schematic diagram of the cell-free system. (B) Low pH-dependent membrane fusion and added magnesium ions and dNTPs are critical for ASLV early DNA production. 293(TVA800) cells were challenged with RCASBP(A)-EGFP at an estimated MOI of 0.15 EFGP transducing unit. The ASLV fusion/uncoating reaction was then set up at 37° C. with 150 µg of 293 S10 fraction and was performed under permissive (3 mM $NH_4Cl$) or nonpermissive (63 mM $NH_4Cl$) conditions for ASLV Env-dependent fusion. Samples were incubated with or without 3 mM $MgCl_2$ and 50 µM dNTPs. Viral DNA was then quantified by using a real-time PCR amplification method. The results are shown as the number of viral DNA molecules synthesized per cell that was used to make the VPNS. A representative example of an experiment that was performed at least three independent times, each time in triplicate, is shown, with the standard deviation of the data indicated with error bars.

FIG. 17. Cellular factor(s) stimulate ASLV fusion/uncoating in the cell-free system. (A) The 293 S10 fraction enhances both the rate and extent of ASLV early viral DNA production. 293(TVA800) cells were challenged with RCASBP(A)-EGFP at an estimated MOI of 0.4 EGFP transducing unit, and fusion/uncoating reactions were set up at 37° C. with 3 mM $NH_4Cl$ and with different amounts (0-350 µg) of 293 S10 fraction added. For control purposes, samples containing the maximum amount of 293 S10 fraction (350 µg) were also incubated under nonpermissive fusion conditions (63 mM $NH_4Cl$ or at 4° C.). Reactions were then stopped at the indicated times and early viral DNA products were measured as in FIG. 16B. A representative example of an experiment that was performed two independent times, each time in triplicate, is shown, with the standard deviation of the data indicated with error bars. (B) ASLV early viral DNA production in the cell-free system is specifically enhanced by a 293 S10 fraction. 293(TVA800) cells were challenged with RCASBP(A)-EGFP at an estimated MOI of 0.1 EGFP transducing unit. The ASLV fusion/uncoating reaction as then set up at 37° C. with 3 mM NH$_4$Cl and with different amounts of the 293 S10 fraction, BSA, or yeast cell S10 fraction added. Early viral DNA products were then measured as in FIG. 16B. A representative example of an experiment that was performed two independent times, each time in triplicate, is shown with the standard deviation of the data indicated with error bars. (C) The 293 cell factor(s) are soluble and >5 kDa in size. 293 (TVA800) cells were challenged with RCASBP(A)-EGFP at an estimated MOI of 0.15 EGFP transducing unit. Fusion/uncoating reactions were then set up at 37° C. with either 150 µg of 293 S10 fraction or equivalent amounts of either 293 P100 or S100 fractions, or 293 S10 fractions that had been subjected to gel filtration ($M_r$>5 kDa), dialysis (molecular mass cutoff, 3.5 kDa) or membrane filtration (molecular mass cutoff, 5 kDa). Early viral DNA products were measured as described in FIG. 16B. The results are shown as a percentage of the data obtained with 150 µg of 293 S10 fraction added (designated as 100%). A representative example of an experiment that was performed twice, both times in triplicate, is shown, with the standard deviation of the data indicated with error bars.

FIG. 18. The 293 S10 factor(s) act after completion of low pH-dependent fusion. (A) ASLV Env-dependent fusion occurs immediately after removal of the NH$_4$Cl-imposed block. 293(TVA800) cells were challenged with RCASBP (A)-EGFP at an estimated MOI of 0.4 EGFP transducing unit. Cell-free ASLV fusion/uncoating reactions were then set up with 150 µg of 293 S10 fraction and 3 mM NH$_4$Cl, and fusion was initiated by temperature shift from 4° C. to 37° C. At different time points, the concentration of NH$_4$Cl was increased to 63 mM to block any further virus-cell membrane fusion. ASLV early viral DNA products were then measured by real-time PCR amplification as described in FIG. 16B. The results are shown relative to those obtained from a parallel sample that was allowed to proceed to completion after the initiation of fusion (defined here as 100%). A representative example of an experiment that was performed twice, each time in triplicate, is shown, with the standard deviation of the data indicated with error bars. (B) The 293 S10 factor(s) act after low pH-dependent membrane fusion has been completed. 293(TVA800) cells were challenged with RCASBP (A)-EGFP at an estimated MOI of 0.08 EGFP transducing unit, and an ASLV cell-free fusion/uncoating reaction was set up with 3 mM HN$_4$Cl and without the 293 S10 fraction. Fusion was induced for 1 minute by shifting the samples to 37° C., and then NH$_4$Cl was added to a final concentration of 63 mM to block any further fusion. Samples were then incubated with or without a 150 µg aliquot of the 293 S10 fraction for an additional 6 hours at 37° C. before early viral DNA products were measured by real-time PCR amplification. The results are shown relative to those obtained from a control sample that had the 293 S10 fraction added before induction of fusion and was maintained under fusion-permissive conditions (3 mM NH$_4$Cl) (defined here as 100%). A representative example of an experiment that was performed three times, each time in triplicate, is shown, with the standard deviation of the data indicated with error bars.

FIG. 19. ATP hydrolysis is required for the 293 S10 fraction-stimulation of ASLV early DNA synthesis. 293 (TVA800) cells were challenged with RCASBP(A)-EGFP at an estimated MOI of 0.15 EGFP transducing unit. Fusion/uncoating reactions were then set up as described for FIG. 16B in the presence of 150 µg of 293 S10 fraction and with or without 2.5 mM adenosine 5'-[γ-thio]triphosphate (A). Alternatively, 10 units/ml apyrase was added to reaction samples at the indicated times after shifting to 37° C. (B). After a 6 hour incubation, early viral DNA was quantified by real-time PCR amplification as in FIG. 16B. A representative experiment performed in triplicate is shown, with the standard deviation of the data indicated by error bars.

FIG. 20. A 293 cell nuclear extract promotes late ASLV DNA synthesis. 293(TVA800) cells were challenged with RCASBP(A)-EGFP at an estimated MOI of 1.0 EGFP transducing unit. Fusion/uncoating reactions were then set up at 37° C. with 150 µg of 293 S10 fractions, 3 or 63 mM NH$_4$Cl, and either with (+) or without (−) 1.6×10$^6$ cell equivalents of a 293 cell nuclear extract. Approximately 20 hours later, early (A) and late (B) ASLV DNA products were measured by real-time PCR analysis. An experiment that was performed in triplicate is shown with the standard deviation of the data indicated with error bars. A similar ratio of early/late viral DNA molecules (600:1) was observed in a separate experiment that was performed in triplicate under the same conditions, except at a 20-fold lower apparent MOI (data not shown).

FIG. 21. Cellular factors stimulate HIV-1 uncoating in the cell-free system. (A) The 293 S10 fraction stimulates HIV-1 early DNA synthesis from a pseudotyped HIV-1 [EnvA] vector. An HIV [EnvA] fusion/uncoating assay was set up at 37° C. as described in Experimental Procedures with (+) or without (−) 100 µg 293 S10 fraction or dNTPs and with either 3 mM or 63 mM NH$_4$Cl. HIV-1 viral DNA was quantified by real-time PCR amplification. The results are shown as viral DNA molecules accumulated per cell used to generate the VPNS. A representative example of an experiment that was performed at least three independent times, each time in triplicate, is shown with the standard deviation of the data indicated with error bars. (B) The 293 cell factor(s) are larger than 5 kDa in size. An HIV [EnvA] fusion/uncoating assay was set up at 37° C. with either 3 mM or 63 mM NH$_4$Cl and with either 200 µg of complete 293 S10 fraction or an equivalent amount of 293 S10 fraction that had been subjected to gel filtration (Mr>5 kDa). HIV-1 viral DNA was quantified by real-time PCR amplification. The results are shown as viral DNA molecules accumulated per cell used to generate the VPNS. A representative example of an experiment that was performed twice, each time in triplicate, is shown with the standard deviation of the data indicated with error bars.

FIG. 22. Reconstitution of Cyclosporin A-inhibition and Lv-1 restriction of early HIV-1 DNA synthesis in the cell-free system. HIV [EnvA] cell-free fusion/uncoating reactions were set up as described for FIG. 21. (A) Reactions contained 150 µg 293 S10 fraction and 3 mM NH$_4$Cl with or without 20 µM cyclosporin A added before the temperature shift to 37° C. (B) Reactions contained 50 µg 293 S10 fraction and 3 mM NH$_4$Cl with increasing amounts of S10 fractions from 293 cells, CV-1 cells, or FrHL-2 cells. Following these reactions viral DNA was quantified by real-time PCR amplification and the numbers of DNA molecules that were produced per cell used to generate the VPNS are shown. Representative examples of experiments that were performed at least two times, each time in triplicate, are shown with the standard deviation of the data indicated with error bars.

Figure 23:
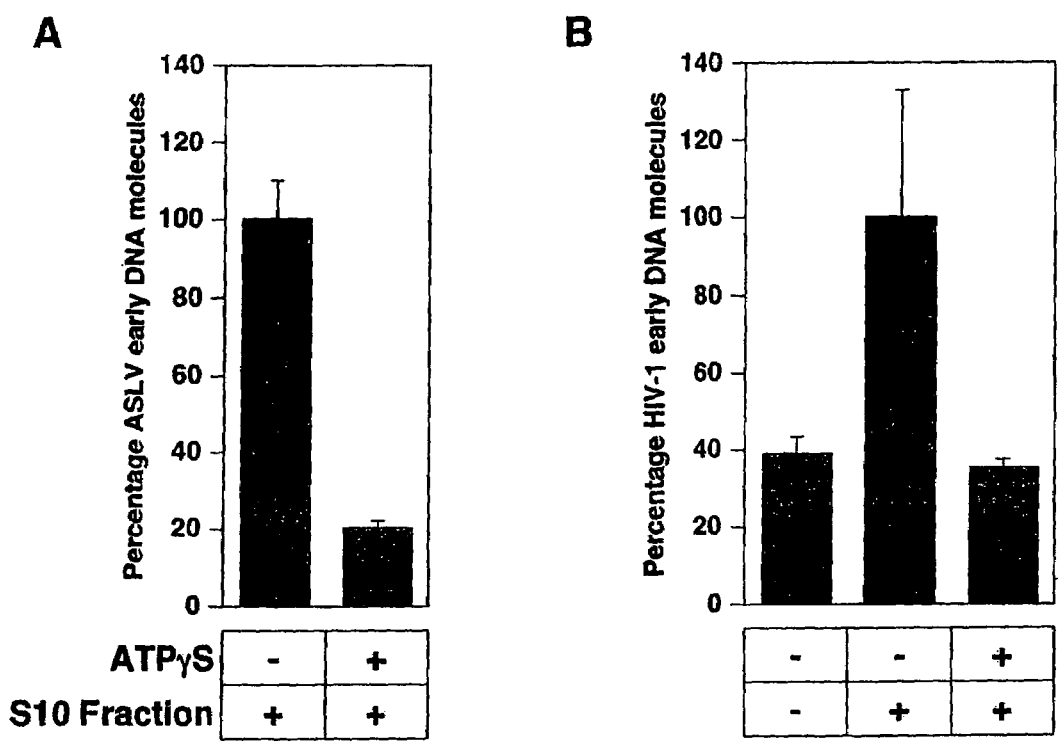

FIG. 23. ATP hydrolysis is required for the 293 S10 fraction-stimulation of ASLV and HIV-1 early DNA synthesis. Cell-free fusion and uncoating reactions were set up with either ASLV-A (panel A) or HIV [EnvA] (panel B) as described for FIGS. 1 and 3, respectively. ASLV-A-containing reactions included 150 µg 293 S10 fraction with or without 2.5 mM ATPγS, and the HIV [EnvA]-containing reactions included 200 μg 293 S10 fraction with or without 4.5 mM ATPγS. After a 6-hour incubation, viral DNA was quantified by real-time PCR amplification. The results are shown as percent viral DNA molecules accumulated relative to the amount that was produced without ATPγS. A representative example of an experiment that was performed three times, each time in triplicate, is shown with the standard deviation of the data indicated with error bars.

DETAILED DESCRIPTION OF THE INVENTION

Figure 1:
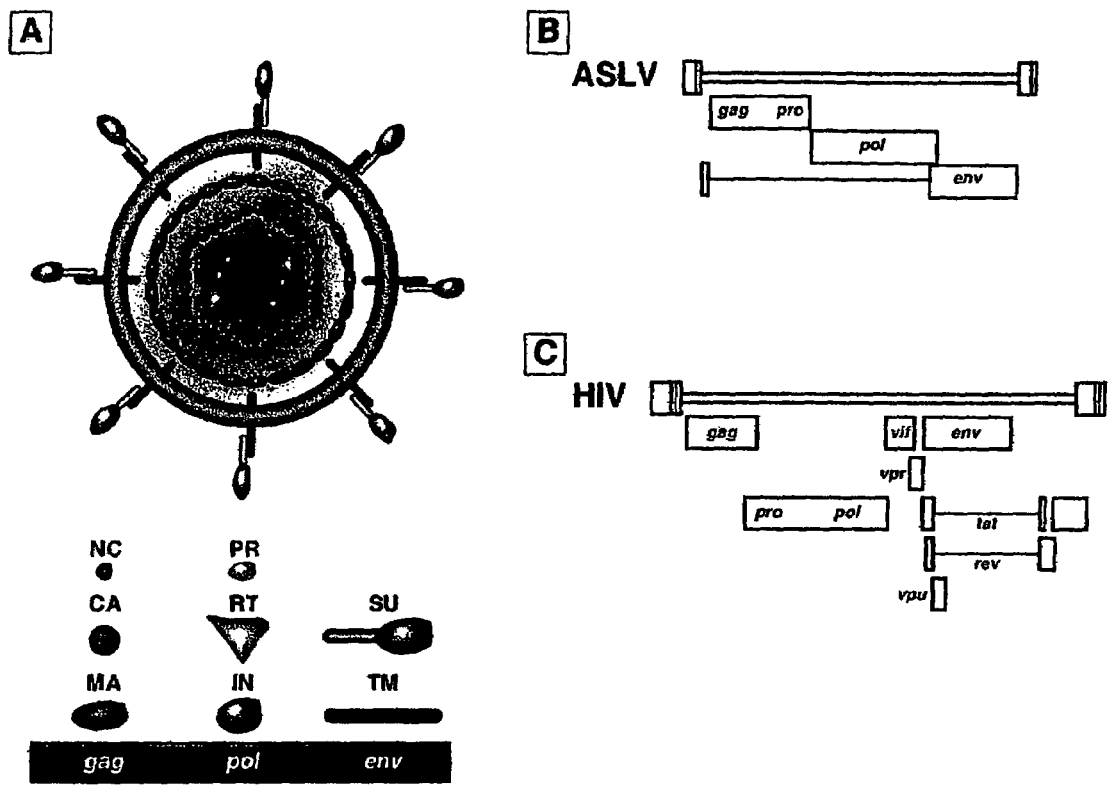
FIG. 1. Retroviral particle structure and genomic organization. A) A representation of a mature avian sarcoma and leukosis virus (ASLV) virion; the individual proteins found in the mature virion are shown schematically. The outer membrane of the virion contains the transmembrane protein (TM), which is associated with the surface subunit (SU). The matrix protein (MA) lies just under this outer membrane. Capsid (CA) is the major structural component of the virion core. Inside the core are two viral RNA genomes, partially covered with nucleocapsid protein (NC). The core also contains reverse transcriptase (RT), integrase (IN), and protease (PR). B) ASLV coding regions: the genomic organization of a simple retrovirus. The genetic map of ASLV contains four major coding regions, gag, pro, pol, and env. Different reading frames are indicated by displacement of the genes. C) HIV coding regions: the genomic organization of a complex retrovirus. The genetic map of the human immunodeficiency virus (HIV) contains, besides the major coding regions, information for regulatory proteins (Vif, Vpr, Tat, Nef, Rev, and Vpu). Different reading frames are indicated by displacement of the genes.

Retroviral Particle Structure and Genome Organization. Retroviral particles contain an RNA genome of 7-12 kb packaged within a protein core. This core is surrounded by a membrane lipid bilayer embedded in which is the viral envelope glycoprotein (FIG. 1). The genome contains three major coding regions encoding polyproteins: gag encodes matrix (MA), proteins that form the core [capsid (CA) and nucleocapsid (NC)], and in some retroviruses, small peptides of poorly defined function; pol encodes the reverse transcriptase (RT) and integrase enzymes; and env encodes the surface (SU) and transmembrane (TM) subunits of the viral envelope protein (Env). In addition, retroviruses contain pro which encodes the viral protease responsible for proteolytic processing of the polyproteins (Coffin et al., 1997). Retroviruses are broadly categorized as simple or complex, the latter group containing genes, in addition to those described above, encoding regulatory proteins that further modulate virus-host interactions. Certain simple retroviral genomes also contain viral oncogenes. The two retroviruses discussed in this thesis are the avian sarcoma and leukosis viruses (ASLV), a family of simple retroviruses, and HIV-1, which is a complex retrovirus.

Figure 2:
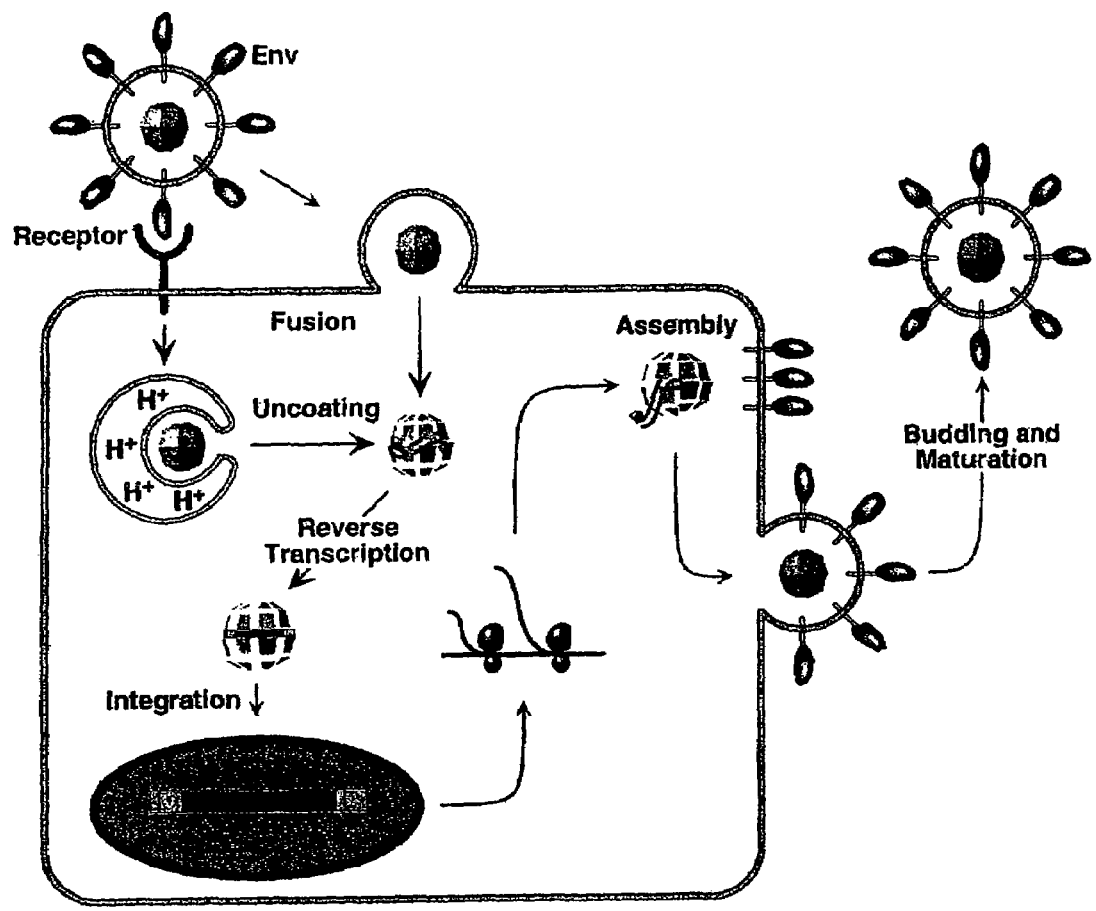
FIG. 2. Retroviral life cycle. The infection process begins following binding of a retrovirus to its target cell. Env-receptor interactions lead to fusion of the viral envelope and the target cell membrane either at the cell surface or from intracellular acidic compartments. The retroviral core, once deposited into the cytosol of the host cell, is proposed to undergo a disassembly step termed uncoating resulting in the activation of reverse transcription. Reverse transcription of the RNA genome is followed by trafficking of the nucleoprotein complex to the host cell nucleus where the viral DNA is integrated into the host genome using the virally encoded IN enzyme. The integrated DNA genome (the provirus) is the template for production of nascent retroviral genomes as well as mRNAs that give rise to all the retroviral-encoded proteins. Production of retroviral particles takes place in the infected host cytoplasm and involves the assembly of Gag and Pol proteins, packaging or RNA genomes and budding to give rise to enveloped virions, thus completing the retroviral life cycle.
Figure 3:
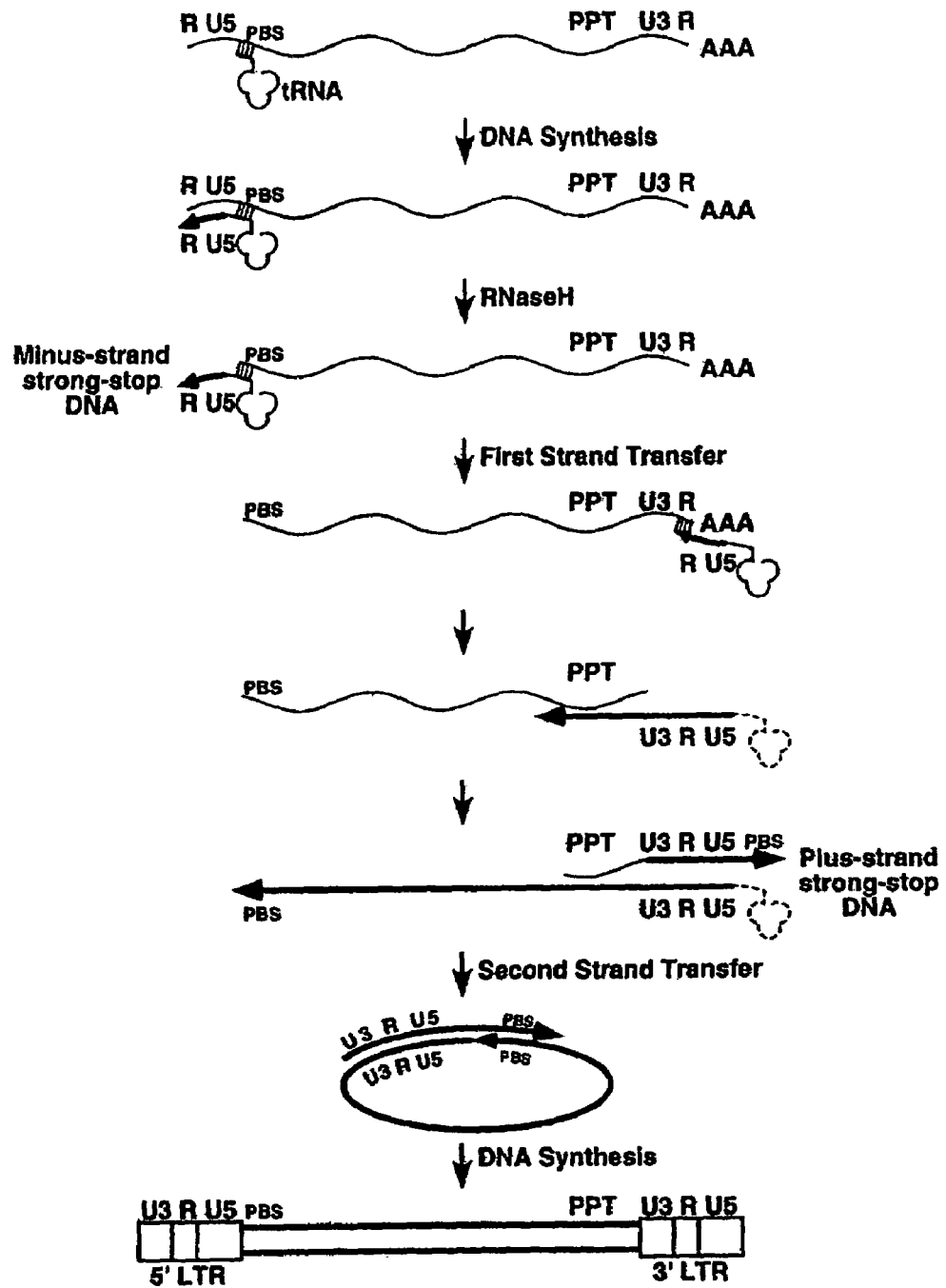
FIG. 3. Mechanism of reverse transcription. The incoming RNA genome (squiggled line) is pre-bound to a tRNA molecule that serves as a primer for RT-mediated synthesis of retroviral DNA (dark solid line). The RNaseH activity of RT mediates the degradation of the viral RNA after it has been reverse transcribed. At two points during reverse transcription, the nascent DNA strand must transfer templates. The RT products generated before these transfer steps are the minus-strand strong stop DNA (−sssDNA) and plus-strand strong stop DNA (+sssDNA). Completion of reverse transcription results in a double-stranded, linear DNA viral genome containing duplications of the DNA ends known as long terminal repeats (LTR). The LTRs contain sequences designated U3, R, and U5. PBS=primer binding site, PPT=polypurine tract.

The Retroviral Life Cycle. The retroviral life cycle begins with attachment of virions to cells via specific interactions between Env and cell-surface receptors leading to the fusion of viral and cellular membranes (FIG. 2). Upon fusion, the core enters the cytoplasm and undergoes uncoating to form the reverse transcription complex (RTC). While the molecular events that occur during this step of the life cycle remain unknown, uncoating ultimately results in reverse transcription of the RNA genome into double-stranded DNA. Reverse transcription is catalyzed by the viral RT and involves the enzyme making two strand-transfers during DNA synthesis resulting in duplication of the DNA ends known as long terminal repeats (LTR) (FIG. 3). Reverse transcription is completed in the cytoplasm for most retroviruses, and is coincident with maturation of the RTC into the pre-integration complex (PIC).

The PIC then transports the viral DNA into the nucleus where the DNA is integrated into the host cell genome in a reaction catalyzed by the viral integrase. The integrated viral DNA, termed the provirus, is maintained as a host cell gene for the rest of the organism's life. The host cell machinery is used for transcription (via a promoter present in the 5' LTR) and splicing of viral genes as well as for synthesis of unspliced, genome length viral RNA. These RNAs are exported to the cytoplasm and used for translation of viral polyproteins that assemble, together with viral genomic RNA, into nascent viral cores at the plasma membrane. Viral envelope proteins are independently expressed and transported to the plasma membrane where cores bud out of the cell. This process results in the virus creating its envelope by acquiring part of the cellular plasma membrane. Viral budding is coincident with proteolytic processing of the precursor polyproteins by the viral protease, and this is the final step in the formation of newly infectious virions. My graduate work has focused on understanding how retroviruses enter cells and undergo fusion and uncoating.

Retroviral Entry

Viral Membrane Fusion. To be able to initiate replication, all enveloped viruses must first fuse their outer membrane with that of the cell in a reaction that is catalyzed by the viral envelope protein. For retroviruses, this is accomplished by the Env protein, which is synthesized as a precursor protein and then cleaved into SU and TM subunits that remain associated. Env is glycosylated and assembles as higher order oligomers. The TM subunit anchors Env in the viral membrane, whereas SU contains receptor-binding determinants and allows virus attachment to the surface of the host cell. Generally, the TM sequence also contains two heptad repeat domains (N- and C-terminal) and a short stretch of hydrophobic residues known as the 'fusion peptide' which is required for mediating membrane fusion (Eckert et al., 2001).

High-resolution crystal structures now exist for envelope proteins from several virus families including the retroviruses (Chan et al., 1997; Weissenhorn et al., 1997), orthomyxoviruses (Bullough et al., 1994; Chen et al., 1999a), paramyxoviruses (Baker et al., 1999), and filoviruses (Malashkevich et al., 1999; Weissenhorn et al., 1998). These proteins seem to have a remarkably conserved tertiary structure, and together with biochemical and mutagenesis experiments, suggest that a common mechanism may be employed for membrane fusion by diverse enveloped viruses. Extensive work with the Influenza and HIV envelope proteins as model systems has led to the proposal of a generalized model for viral fusion (Eckert et al., 2001; Pierson et al., 2003; Skehel et al., 2000).

Figure 4:
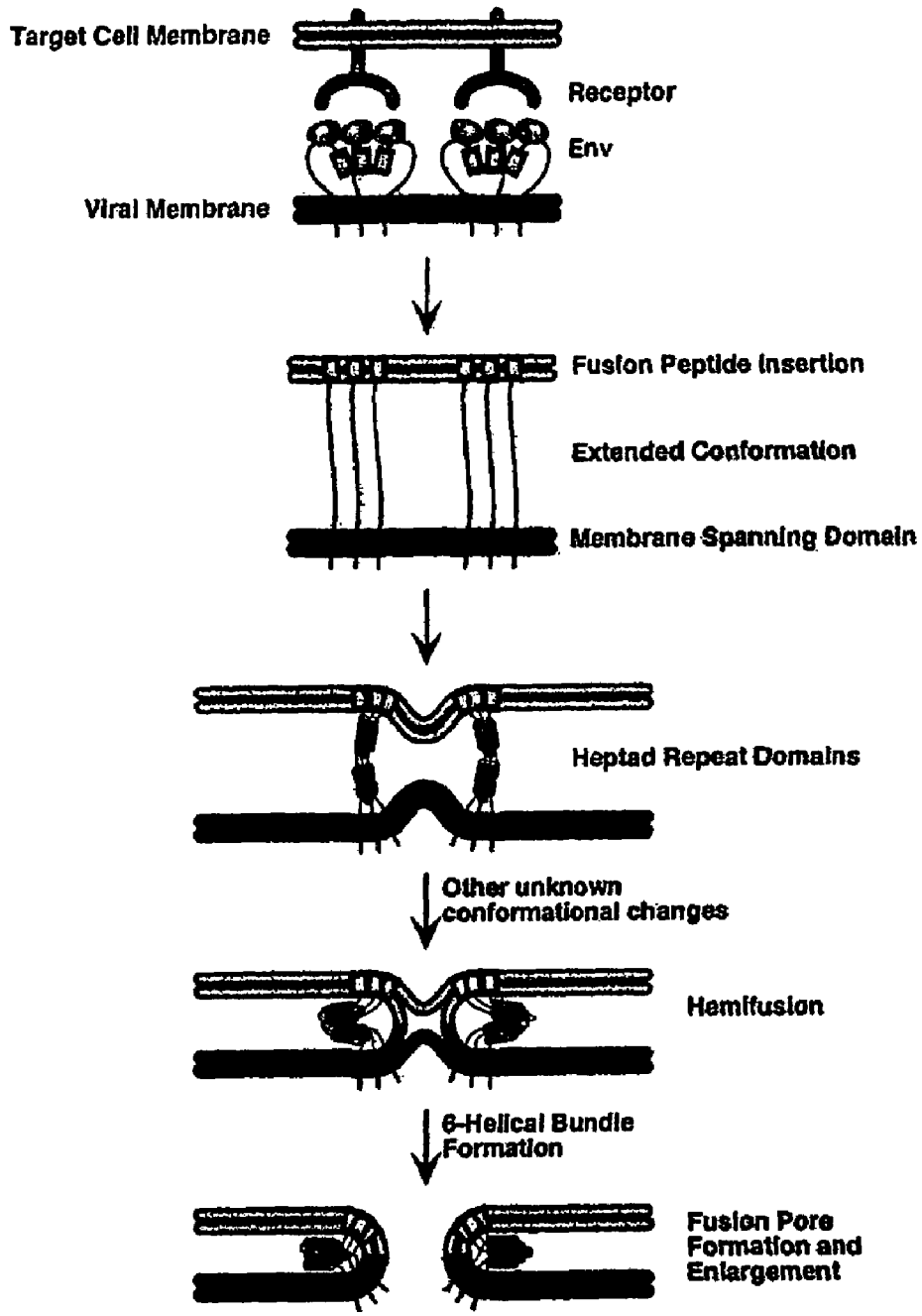
FIG. 4. Model for Env-mediated membrane fusion. Env initially exists in the viral membrane in a 'metastable' state in which the hydrophobic fusion peptide is buried within the interior of the protein. Once Env is triggered for fusion, a first set of conformational changes causes exposure of the fusion peptide and its insertion into the target cell membrane, allowing Env to span both viral and cellular membranes in this extended conformation. A second set of conformational changes then causes a reorientation of Env such that the fusion peptide is forced back into close proximity with the membrane-spanning domain of TM, thereby causing contact between the viral and cellular membranes. This state allows for lipid mixing between the outer leaflets of the two membranes and is termed hemifusion. A third, final set of conformational changes in Env then results in the formation of a closely packed, thermostable, six-helix bundle due to the association of the N- and C-terminal heptad repeat domains of TM. This results in the complete fusion of the two lipid bilayers leading to the formation of a flickering fusion pore. This pore then expands allowing for delivering of the viral core to the cytoplasm.

This model proposes that viral fusion occurs via a series of carefully orchestrated conformational changes in Env resulting in the bringing together of viral and cellular membranes (FIG. 4). Upon proteolytic processing, Env initially exists in the viral membrane in a 'metastable' state in which the hydrophobic fusion peptide is buried within the interior of the protein. Once Env is triggered for fusion, a first set of conformational changes is believed to cause exposure of the fusion peptide and its insertion into the target cell's membrane. Thus, Env spans both viral and cellular membranes in this extended conformation. A second set of conformational changes then causes a reorientation of Env such that the fusion peptide is forced back into close proximity with the membrane-spanning domain of TM, thereby causing contact between the viral and cellular membranes. This state promotes lipid mixing between the outer leaflets of the two lipid bilayers and is termed hemifusion. A third, final set of conformational changes in Env then results in the formation of a closely packed, thermostable, six-helix bundle due to the association of the N- and C-terminal heptad repeat domains of TM. It is believed that the energy released in the formation of this stable six-helix bundle is used to bring the viral and cellular membranes even closer, thus resulting in the complete fusion of the two lipid bilayers and formation of a flickering fusion pore. This pore is thought to then expand allowing delivery of the viral core to the cytoplasm (Eckert et al., 2001; Skehel et al., 2000). Based on this model, peptides that correspond to the heptad repeat domains of HIV-1 Env can inhibit formation of the six-helix bundle in a dominant-negative manner, thereby inhibiting fusion (Pierson et al., 2003). The general process of fusing two membranes seems to be evolutionarily conserved since the mechanisms involved in viral membrane fusion have a remarkable similarity to those of membrane fusion events that occur between organelles within a cell (Chen et al., 2001; Hernandez et al., 1996b).

Mechanisms of Activating Viral Envelope Proteins. To ensure that membrane fusion is not initiated prematurely, the envelope glycoprotein exists on the viral membrane in a metastable state. To initiate infection, the envelope proteins need to be activated to trigger the cascade of conformational changes described above that result in membrane fusion. It is believed that this activation step ultimately serves to destabilize the envelope protein, thereby allowing it to overcome the kinetic barrier that separates its metastable and final fusogenic conformations (Carr et al., 1997).

Figure 5:
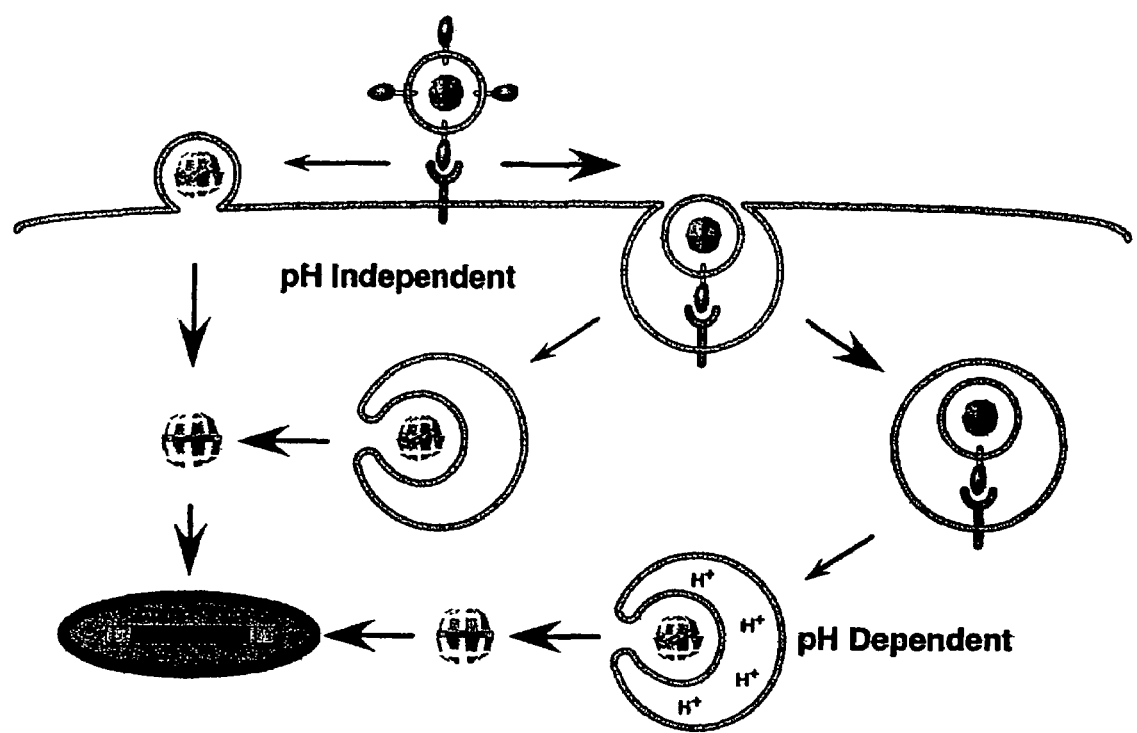

It is believed that viral envelope proteins are activated by either of two physiological signals (FIG. 5). For viruses like Influenza A, activation occurs by exposure of the viral envelope proteins to the low pH environment of acidic intracellular organelles following receptor-mediated endocytosis (Marsh et al., 1989). The only function of the cellular receptor in this case is to allow virus attachment to the cell surface prior to endocytosis. In contrast, the envelope proteins of pH-independent viruses, like those of most retroviruses, are activated by interactions with the cellular receptor, and in some cases by additional interactions with co-receptors. Thus, in the case of pH-independent viruses, cellular receptors function to allow both virus attachment and envelope activation. Therefore, most pH-independent viruses are thought to fuse at the cell surface. It should be reiterated that while pH-dependent and pH-independent envelope proteins defer in their signals for activating fusion, the basic mechanism of the fusion reactions mediated by these proteins are likely very similar. This idea is strongly supported by biochemical, genetic and structural studies with the pH-dependent Influenza and pH-independent HIV-1 envelope proteins (Eckert et al., 2001). The difference in the mode of activating the envelope protein however dictates the location within the cell at which viral fusion occurs i.e. either at the plasma membrane or from an acid intracellular compartment.

Endocytic Pathways used by Viruses to Enter Cells. Cells internalize substances from their environment via endocytosis, and viruses that require low pH for fusion seem to have evolved to access acidic intracellular compartments by utilizing these cellular internalization pathways. For example, most extracellular ligands enter cells by receptor-mediated endocytosis after binding specific cell-surface receptors (Mukherjee et al., 1997). Viruses seem to have evolved to bind these cell-surface receptors and thus take advantage of these ligand-internalization routes. In this way, not only are the viruses able to access low pH environments, but particles are also carried through protective barriers that exist between the plasma membrane and the cytoplasm, such as cortical actin filaments (Schafer, 2002). Importantly, viruses seem to function as inert cargo while being internalized, and thus have been successfully used as probes to characterize mechanisms of cellular endocytosis (Pelkmans et al., 2003).

Figure 6:
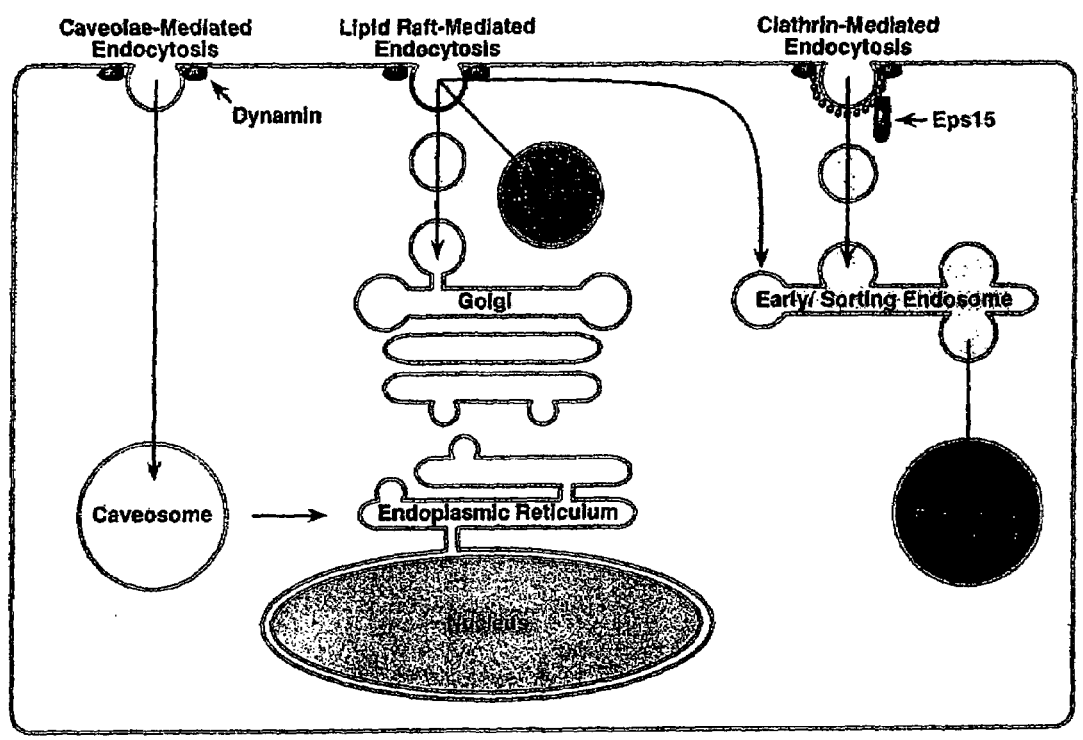
FIG. 6. Cellular endocytic pathways. At least three independent endocytic pathways exist in most cells: clathrin-mediated endocytosis, lipid raft-mediated endocytosis, and caveolae-mediated endocytosis. All three processes begin with the formation of cell surface pits that capture extracellular molecules, but the mechanisms used to create the different pits seem to differ. For example, expression of mutant versions of the protein Eps 15 specifically inhibits clathrin-mediated endocytosis, suggesting the exclusive use of Eps 15 in this pathway. However, in all three pathways, these pits invaginate and are 'pinched-off' from the plasma membrane by the protein dynamin to form intracellular transport vesicles. Thus, expression of dynamin mutants inhibits internalization via all three pathways in a dominant negative manner. The different pit-derived vesicles formed at the cell surface are transported to different intracellular organelles, including novel compartments like the caveosome. It was been inferred that different kinds of lipid raft-mediated endocytic pathways exist in cells since markers of such pathways are trafficked to different final destinations in the cell. Such data have also led to the hypothesis that the various cellular endocytic pathways may be interconnected.

Entry of a virus into a cell can be thought of as occurring in two stages: 1) upon binding the receptor, the virus is initially sequestered and internalized in plasma membrane pits that pinch-off to enclose the particle within a vesicle, and 2) trafficking of the vesicle then transports the particle to an intracellular organelle where viral membrane fusion can occur. It is now starting to become clear that many independent internalization mechanisms exist within the cell, and that they funnel into complex, often overlapping trafficking pathways. While the best understood endocytic pathway is that mediated by clathrin, evidence is now emerging for the existence of other pathways such as caveolar endocytosis and lipid-raft mediated endocytosis (FIG. 6).

Clathrin-Mediated Endocytosis. Our clearest understanding of the mechanisms of endocytosis and the intracellular compartments accessed by these pathways comes from studies of clathrin-mediated endocytosis (CME) (for recent reviews see (Conner et al., 2003; Mousavi et al., 2003)). In general, CME is kinetically rapid with half-times of internalization in the range of 5-30 minutes (Mukherjee et al., 1997). CME begins with cytosolic coat proteins forming an electron-dense, 'coated pit' at the cell surface. Clathrin, a major component of the coat, exists as a triskelion structure that is induced to self-assemble into cage-like structures by the other major constituent of the coat, the adaptor protein (AP) 2 complex (Brodsky et al., 2001). Subunits of the AP2 complex dictate the site of coat assembly on the plasma membrane, interact with clathrin to initiate the assembly process, and bind internalization signals within receptors concentrating them within the cage (Kirchhausen, 1999). Assembly of the cage is thought to induce membrane curvature leading to the formation of a pit, and the GTPase, dynamin, is then recruited to form a 'collar' around the neck of the coated pit, pinching it off to create a clathrin-coated vesicle (FIG. 6). Interaction of this basic machinery with accessory proteins, such as Eps15, spatially and temporally regulates the process of CME (Conner et al., 2003).

Upon leaving the cell surface, clathrin-coated vesicles are stripped of their coat proteins and fuse with early endosomes. Here, the internalized cargo is sorted for transport to other locations in the cell including the TGN, the ER, and back to the plasma membrane (Gruenberg, 2001). However, most internalized cargo from the early endosome ends up reaching late endosomes and lysosomes via a continuum of tubular and vesicular intermediates. The lumen of this intracellular endosomal system becomes progressively more acidic during transport, thereby promoting dissociation of internalized receptors from their ligands (Mukherjee et al., 1997). Endosomes are also highly enriched in degradative enzymes that break down the ligands into core components for use by the cell, while the receptors are recycled back to the plasma membrane for successive rounds of internalization (Gruenberg, 2001).

Over-expression of mutant forms of dynamin or Eps15 seem to inhibit CME in a dominant-negative manner (Benmerah et al., 1999; Damke et al., 1994), and such cell-biological tools have now been used to show that several different viruses use CME to enter target cells (DeTulleo et al., 1998; Diaz-Griffero et al., 2002; Joki-Korpela et al., 2001; Pho et al., 2000; Snyers et al., 2003). Such viruses may have evolved to take advantage of the low pH they encounter within endosomes to trigger the membrane fusion reaction, perhaps to avoid being degraded by the endosomal degradative enzymes. In support of this idea, if low pH-dependent viruses are trapped within endosomes prior to fusion by neutralizing endosomal pH with lysosomotropic agents such as ammonium chloride ($NH_4Cl$), they are degraded, and this has become a commonly used criterion for classifying viruses as low pH-dependent (Marsh et al., 1989).

Caveolae-Mediated Endocytosis. Recently, the Simian Virus 40 (SV40) has been elegantly used as a probe to characterize caveolar endocytosis (Pelkmans et al., 2003). SV40 enters cells via small, tight-fitting invaginations at the plasma membrane termed caveolae (Anderson et al., 1996). Unlike clathrin-coated pits, caveolae do not seem to be surrounded by an electron-dense coat, but rather by a scaffold formed by the protein caveolin-1 (Anderson, 1998). Caveolar endocytosis is also kinetically much slower than CME, with half times of internalization often ranging from 30 minutes to several hours (Anderson, 1998). Binding of SV40 to its cell-surface receptor, the MHC class I molecule, seems to induce receptor clustering in lipid rafts and recruitment of caveolin-1-positive vesicles from the cytoplasm (Anderson et al., 1998; Pelkmans et al., 2001). These vesicles fuse with the plasma membrane to form caveolae, and thus, caveolae are sometimes operationally defined as a specific type of lipid raft (Kurzchalia et al., 1999). Caveolae formation is thought to trigger a signal transduction event involving local tyrosine phosphorylation, depolymerisation of the actin cortical filaments and production of phosphatidylinositol 4,5-bisphosphate. These events lead to recruitment of dynamin-2 and pinching-off of SV40-containing caveolae (Pelkmans et al., 2002). These vesicles are then trafficked to and fuse with a newly discovered intracellular organelle, the caveosome, which seems devoid of markers of the biosynthetic and endocytic system, and unlike endosomes, has a neutral pH environment (Pelkmans et al., 2001). Here, SV40 particles are sorted into caveolin-1-negative tubules that are transported via microtubules to the ER from where the virus then enters the cytoplasm. Although many details remain to be determined including whether the caveosomal and endosomal systems communicate, these studies strengthen the case for using viruses as probes to dissect endocytic mechanisms.

Lipid Raft-Mediated Endocytosis. In addition to clathrin and caveolae-mediated endocytosis, lipid rafts at the cell surface seem to mediate a variety of different endocytic pathways (for recent reviews see (Nichols et al., 2001; Sharma et al., 2002)). Lipid rafts have been operationally defined as detergent-resistant, membrane microdomains structurally composed of cholesterol and glycoshpingolipids and are highly enriched in glycosylphosphatidylinositol (GPI)-anchored as well as other lipid-anchored proteins (Brown et al., 1998; Simons et al., 1997). To analyze lipid raft-mediated endocytosis, recent approaches have combined the use of GPI-anchored proteins as markers for lipid rafts with cholesterol-depleting drugs like methyl-$\beta$-cyclodextrin, which disrupts raft structure. In general, such pathways seem to function independently of the machinery involved in CME. For example, the GPI-anchored proteins CD59 as well as a GPI-anchored version of GFP both enter cells through a slow, constitutive pathway that delivers them to the Golgi via intracellular transport vesicles devoid of classical endosomal markers (Nichols et al., 2001). Disrupting CME via the expression of dominant negative Eps15 has no effect on internalization via this pathway. Several bacterial toxins that enter cells by binding cell surface glycosphingolipids also seem to use this pathway for delivery to the Golgi (Mallard et al., 1998; Orlandi et al., 1998). However, other cell surface GPI-anchored proteins such as CD55 or the folate receptor seem to be trafficked to the recycling endosome rather than to the Golgi (Chatterjee et al., 2001). This lipid raft-dependent pathway also seems to be clathrin-independent and may be regulated by the Rho family GTPase cdc42 (Sabharanjak et al., 2002). A third, distinct lipid raft-dependent internalization pathway delivers another raft marker, Interleukin-2 receptor, to as yet unidentified intracellular compartments and then to the lysosome (Lamaze et al., 2001). While this pathway is also clathrin-independent, it seems to be triggered by ubiquitination, is dependent on dynamin and is regulated by Rho GTPase family members other than cdc42. It remains unknown whether these different lipid raft-mediated endocytic pathways communicate with each other and with clathrin and caveolae-mediated pathways.

Recent evidence suggests that several viruses use lipid rafts during various stages of their life cycles, including endocytosis to access intracellular low pH compartments (Chazal et al., 2003). For example, the cell surface receptors for the ecotropic strain of the retrovirus Murine Leukemia Virus (MLV) as well as receptors for the Ebola and Marburg filoviruses are found in plasma membrane lipid rafts (Chan et al., 2001; Lu et al., 2000). These viruses fuse out of endosomes in a low pH-dependent manner, and disrupting lipid raft structure with cholesterol-depletion has been shown to inhibit viral entry (Empig et al., 2002; Lu et al., 2002). However, it remains unknown whether these viruses use one of the known lipid raft-mediated endocytic pathways, or an as yet unidentified pathway. As the molecular mechanisms of these pathways are elucidated and dominant negative inhibitors of these pathways are created, more viruses are sure to be identified that use lipid raft-mediated endocytosis.

Retroviral Uncoating.

Figure 7:
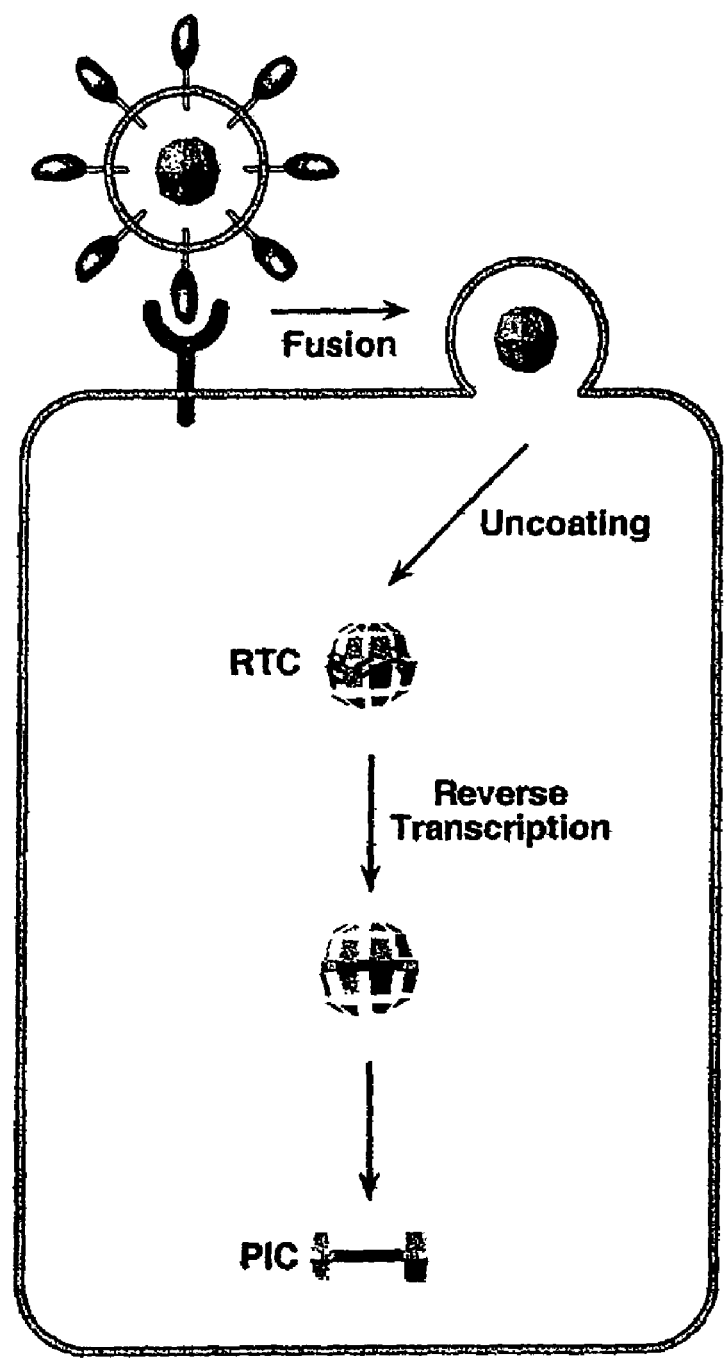
FIG. 7. Retroviral uncoating. Outside the cell, the viral core functions to protect and transport the genome, but once membrane fusion has occurred, the core is delivered to the cytoplasm and must undergo biochemical changes to initiate genome replication. This transformation of the core is termed uncoating and results in the formation of the reverse transcription complex (RTC). Coincident with completion of reverse transcription, the RTC matures into the pre-integration complex (PIC).

Outside the cell, the viral core functions to protect and transport the genome. But upon membrane fusion, the viral core is delivered to the cytoplasm and must then undergo biochemical changes to initiate genome replication. This transformation of the core is termed viral uncoating. In the case of retroviruses, upon fusion, the viral core is converted to the reverse transcription complex (RTC) that creates double stranded DNA from the RNA genome (FIG. 7). The RTC is then thought to mature into the pre-integration complex (PIC). The molecular mechanisms leading to the formation of the RTC and initiation of reverse transcription remain one of the least understood aspects of the retroviral life cycle. In fact, the mechanisms of uncoating for almost all enveloped viruses have remained a fundamental unsolved problem in virology, primarily due to the lack of appropriate biochemical uncoating assays.

Biochemical Changes in the Viral Core during Uncoating. It has been hypothesized that part of the biochemical mechanism of viral uncoating may involve an ordered, disintegration of the viral core to form a sub-viral structure that can function to initiate genome replication (Whittaker et al., 2000; Young, 2001). General support for this hypothesis comes from experiments with the influenza virus (Helenius, 1992). Influenza virus particles enter cells by receptor-mediated endocytosis followed by low pH-activated fusion out of late endosomes (Matlin et al., 1982; Sieczkarski et al., 2002). As particles pass through endosomes prior to fusion, it is thought that the M2 viral membrane protein functions as a proton-pump to acidify the interior of the virus (Pinto et al., 1992). This drop in pH causes conformational changes in M1, the viral structural protein that forms the exterior of the viral ribonucleoprotein core, causing it to dissociate from the core (Bui et al., 1996). Interestingly, this disintegration process is only completed once membrane fusion occurs and the sub-viral core is deposited in the cytoplasm. Completion of uncoating leads to transport of the viral genome to the nucleus where replication begins (Martin et al., 1991a; Martin et al., 1991b). While low pH functions to initiate Influenza uncoating, it remains unknown how this process is completed once the core is deposited in the cytoplasm.

As with Influenza, current models suggest that the retroviral core sheds some of its components during the formation of the pre-integration complex (PIC) (Dvorin et al., 2003; Goff, 2001). The primary approach that has been used to try to characterize both RTC and PIC formation has been to examine biochemically purified retroviral complexes from cells early after initiating infection. Intracellular retroviral complexes of varying compositions have been described, but in general, such studies have indicated that the core of HIV-1 sheds most of its CA and NC proteins at some point after fusion (Bukrinsky et al., 1992; Bukrinsky et al., 1993; Farnet et al., 1991; Fassati et al., 2001; Karageorgos et al., 1993; Miller et al., 1997). However, this does not seem to be the case for MLV (Bowerman et al., 1989; Fassati et al., 1999; Li et al., 2001). Some of these sub-viral complexes also contain varying amounts of cellular proteins thought to be important in nuclear import and integration of viral DNA including importin-α, histones, the transcriptional regulator HMG I(Y), the non-homologous end joining proteins Ku70 and Ku90, and chromatin remodeling proteins like the integrase interacting protein Ini1. Such studies have also suggested that the HIV-1 PIC is transported to the nucleus via functionally overlapping nuclear localization signals in the viral MA, IN, and Vpr proteins, as well as the viral DNA flap produced during reverse transcription (Dvorin et al., 2003). However, a major caveat of using such biochemical approaches has been that since retroviruses have a very low infectious to physical titer (on average only 1 in 1,000 particles is infectious (Coffin et al., 1997)), the vast majority of these observed sub-viral complexes must represent viruses on a non-productive route of infection. This caveat has been somewhat addressed by using cell-free assays that reconstitute retroviral integration in vitro to show that some of these complexes from cells are competent to mediate integration, thus functionally defining them as PICs (Brown et al., 1987; Coffin et al., 1997).

It has been more difficult to biochemically define viral intermediates that form immediately after fusion (such as the RTC) because of the lack of an assay that reconstitutes retroviral fusion and uncoating in vitro. Instead, experiments in which viral complexes were partially purified from cells early after initiating acute infection have suggested that 2-3 distinct sub-viral complexes exist within the target cell cytoplasm after fusion in the case of both the retroviruses MLV and HIV-1 (Fassati et al., 1999; Fassati et al., 2001). At least one of these complexes is able to initiate reverse transcription in the endogenous reverse transcription (ERT) reaction. In the ERT reaction, viral particles in solution (or sub-viral complexes in the case of the experiments described above) are treated with weak detergents and high concentrations of dNTPs (i.e., 10-50 fold above physiological levels) to activate the reverse transcriptase activity within the particle (Temin et al., 1972). It is thought that the detergent permeablizes the viral membrane and weakens CA-CA interactions in the core, thereby allowing dNTPs access to RT. However, since ERT activity requires neither viral membrane fusion nor viral uncoating, it remains unclear how the sub-viral complexes described above that were isolated from acutely infected cells relate to the formation of the RTC during an infection. This problem is further compounded by the fact that the majority of the virions are probably on a non-productive route of infection.

Recently, an alternative, cell biological approach has been used to study the functionally relevant dynamic changes in the HIV core after fusion. By using HIV-1 particles that contain a Vpr-GFP fusion protein and microinjecting target cells with fluorescently labeled dNTPs, Hope and colleagues are able to elegantly combine microscopic visualization of an incoming viral particle with synthesis of reverse transcripts in real-time (McDonald et al., 2002). This allows them to identify the RTC in intact cells, and initial experiments have suggested that these complexes use the microtubule cytoskeleton for transport towards the nucleus, consistent with earlier biochemical studies (Bukrinskaya et al., 1998). This approach should prove useful in characterizing changes in the biochemical composition of the retroviral core as it progresses through various stages of uncoating.

Ultimately however, such biochemical or microscopy-based approaches remain descriptive in nature, since the RTC/PIC is observed after being formed. To gain a mechanistic understanding of uncoating, the field needs an in vitro assay that reconstitutes retroviral fusion leading to productive uncoating and reverse transcription. Such an assay would allow us to address fundamental aspects about what is required for uncoating to occur when a virus enters a cell, basic questions that currently remain unanswered.

Viral Mutants Believed to be Defective in Retroviral Uncoating. It has been suggested that certain viral proteins, such as the core structural protein CA and the accessory protein Vif, may function during HIV assembly to ensure that virus particles are assembled in such a manner that they can be uncoated correctly after entering the target cell (Dvorin et al., 2003). For example, biochemical assays that examine the stability of the viral core in vitro have been used to identify CA point mutants that cause the formation of cores with either increased or decreased stability relative to wild type (Cairns et al., 2001; Forshey et al., 2002). In either case, while these viruses do not exhibit defects in core-morphology or core-delivery into the cytoplasm, they are unable to initiate reverse transcription in target cells. Based on recently proposed models for the structure of the HIV core (Li et al., 2000), it has been predicted that these mutations in CA probably disrupt CA-CA interactions, destabilizing the core. This has led to the hypothesis that virion assembly must produce cores with 'optimal' stability for uncoating to occur efficiently (Forshey et al., 2002). It has also been suggested that, in addition to CA structure affecting uncoating, conformational changes in CA may modulate maturation of the RTC. In support of this idea, it has been found that HIV CA is phosphorylated, and mutations that affect phosphorylation inhibit completion of reverse transcription without affecting initiation (Cartier et al., 1999). However, due to the lack of a biochemical uncoating assay, it has not been possible to directly test either of these hypotheses.

Like CA, Vif also seems to modulate virus assembly and thus affect early steps in viral infection. Viruses with vif deletions are unable to accumulate reverse transcripts in cells (Simon et al., 1996; von Schwedler et al., 1993), and cores from these viruses have decreased structural stability (Ohagen et al., 2000). However, recent studies have shown that Vif also suppresses the antiretroviral activity of a cellular cytidine deaminase, APOBEC3G, by inhibiting its incorporation into assembling HIV particles (Sheehy et al., 2002). Upon entry into a target cell, APOBEC3G molecules within Δvif viruses do not inhibit uncoating, but rather cause hypermutation and/or degradation of newly synthesized reverse transcripts (Goff, 2003). Thus, Vif's function in core stability may affect uncoating while its function in inhibiting APOBEC3G incorporation affects a post-reverse transcription step. It remains to be determined how Vif modulates viral core stability and whether these distinct functions of Vif overlap.

Another HIV accessory protein, Nef, seems to be important for uncoating, but not absolutely required. Multiple functions have been ascribed to Nef including down-regulation of several cell surface proteins as well as interaction with cell-signaling molecules, and deleting nef causes an attenuation of HIV pathogenesis in vivo (Geyer et al., 2001). In a single cycle of replication, Δnef viruses are defective at a step after viral entry but prior to completion of reverse transcription consistent with a function for Nef during uncoating (Schwartz et al., 1995). Interestingly, HIV Δnef viruses are no longer defective when their envelope is replaced with that of the low pH-dependent Vesicular Stomatitis Virus (VSV) (Aiken, 1997); this causes the particles to enter cells by endocytosis rather than fusion at the plasma membrane. Current models suggest that Nef may function after HIV fusion at the cell surface to enhance delivery of the viral core through the cortical actin filaments. Viruses entering by endocytosis are transported through such protective barriers while still within the endosome, and thus would not require Nef. However, as is the case for all the viral proteins discussed above, the actual mechanism of Nef action during uncoating remains unknown.

Figure 8:
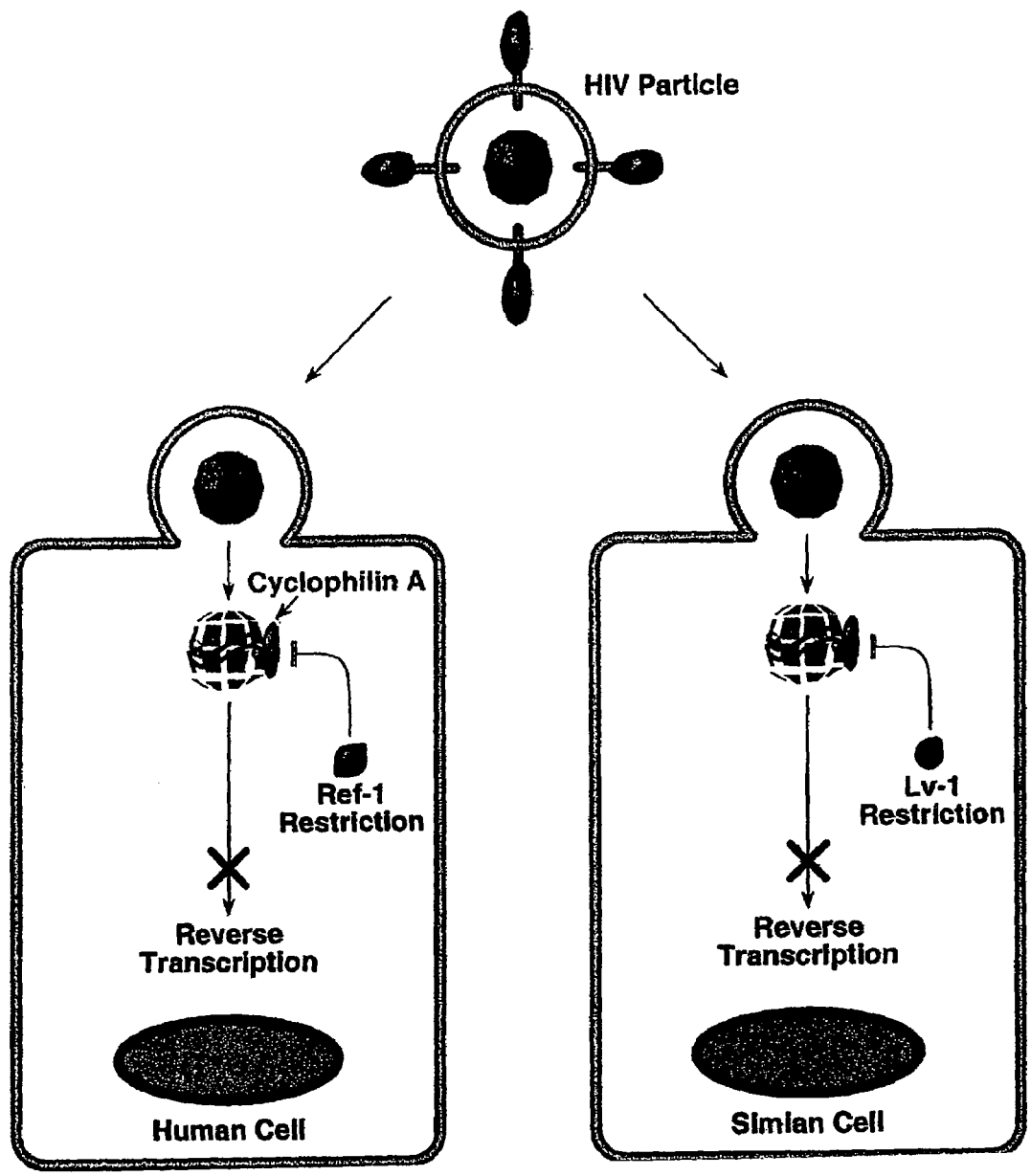
FIG. 8. Cellular restrictions to HIV-1 uncoating. Certain mammalian cells express restriction factors that target the capsid of incoming HIV-1 particles and inhibit reverse transcription. This suggests that these factors act during HIV-1 uncoating. Simian cells express the lentivirus susceptibility-1 (Lv-1) factor, while human cells express the potentially related, restriction factor-1 (Ref-1) (Lv-1/Ref-1 is TRIM5-alpha; Bieniasz, 2004) The extent of inhibition depends upon the particular restriction factor and differs between different cell lines. Cyclophilin A, a cellular factor brought into the cell by the incoming HIV-1 particle, modulates both Ref-1 and Lv-1 restrictions. Specifically, HIV-1 cores lacking functional cyclophilin A are subject to Ref-1 restriction in human cells and overcome Lv-1 restriction in simian cells. In this way, cyclophilin A may help ensure efficient HIV-1 infection of human cells and limit infection in unnatural hosts.

Cellular Restrictions to Early Steps of Retroviral Uncoating. Although upon fusion the retroviral core must almost certainly encounter cellular proteins in the cytoplasm, it remains unknown whether such cellular factors are recruited to the incoming core to function during uncoating. However, recent experiments have suggested that some cells have evolved to express 'restriction factors' that inhibit retroviral infection at a step after cytoplasmic delivery of the core but prior to reverse transcription (FIG. 8) (for review see (Bieniasz, 2003)). This mode of restriction is different from that mediated by APOBEC3G, where inhibition occurs after uncoating and is mediated by a cellular factor that is already present in the virus. For example, it has been found that challenging certain simian cells with HIV-1 results in the delivery of the viral core into the cytoplasm, but reverse transcription is blocked to differing extents in these cells (Besnier et al., 2002; Cowan et al., 2002; Munk et al., 2002). Fusing these simian cells with human cells does not overcome the block to HIV infection suggesting that the restriction phenotype is dominant and implying that the simian factor(s) are naturally occurring inhibitors of HIV uncoating. The factors seem saturable since restriction can be overcome by high multiplicities of infection. The implied simian factor(s) has been termed lentivirus susceptibility factor-1 (Lv-1), and it is believed that Lv-1 restriction may contribute, at least in part, to the inability of creating simian model systems for AIDS pathogenesis studies (Bieniasz, 2003). While the identity of Lv-1 and mechanisms of restriction remain unknown, these studies do provide circumstantial evidence that upon fusion, the retroviral core interacts with cellular factors in the cytoplasm. This idea is further supported by the observation that, in addition to naturally occurring restrictions to retroviral uncoating, mutagenesis has been used to isolate cell lines that are unable to support early steps of retroviral infection prior to reverse transcription (Bradley, 2002; Gao et al., 1999).

Innate cellular restrictions to retroviral infections seem to be a general phenomenon. It is now starting to be appreciated that Lv-1 factors from certain simian species are capable of restricting a variety of different lentiviruses, as well as some strains of MLV (Hatziioannou et al., 2003). Furthermore, human cells also seem capable of restricting infection by certain strains of MLV, and less efficiently, HIV-1 (Towers et al., 2000). The implied human factor(s) has been termed restriction factor-1 (Ref-1). Interestingly, since restriction can be saturated, cross-abrogation studies are starting to show that Lv-1 and Ref-1 have overlapping, but not identical, restriction patterns. Furthermore, different cell types seem to exhibit dramatically different specificities and efficiencies of restriction. Thus, it has been suggested that all restriction factors may come from variant alleles of an ancestral Lv-1-like gene, implying that the basic molecular mechanisms of restriction may be shared amongst different factors (Bieniasz, 2003). In support of this hypothesis, genetic experiments have suggested that the CA protein is the viral target for these various restriction factors (Kootstra et al., 2003). While the identities of Lv-1 and Ref-1 and the molecular mechanisms of restriction remain to be identified, an interesting story is emerging about how Cyclophilin A, a cellular protein that is incorporated into assembling HIV particles, may modulate the interactions between an incoming viral core and host cell restriction factors.

Cyclophilin A, a Cellular Protein Believed to Function During HIV Uncoating. The cellular protein Cyclophilin A was initially identified as a Gag-binding partner in a yeast-two hybrid screen (Luban et al., 1993). Subsequently, it was shown that Cyclophilin A is specifically incorporated into virions during particle assembly by directly binding a proline-rich region within the CA domain of Gag at a ratio of 1 Cyclophilin A: 10 CA molecules (Luban, 1996). Structural studies of this interaction have shown that while most of CA exists as a triangular pyramid of $\alpha$-helices, the Cyclophilin A binding site is formed by an exposed loop thought to be on the outer surface of the viral core that fits snugly into a hydrophobic pocket in Cyclophilin A (Gamble et al., 1996). Cyclosporin A, an immunosuppressant that disrupts this tight interaction between CA and Cyclophilin A, inhibits HIV-1 infection at a step after fusion but prior to initiation of reverse transcription (Braaten et al., 1996; Franke et al., 1994; Thali et al., 1994). It was initially hypothesized that since Cyclophilin A possesses a peptidyl-prolyl cis-trans isomerase activity and catalyzes protein folding in cells, it may help form the HIV-1 RTC by catalyzing disruption of CA-CA interactions during uncoating (Luban, 1996). However, trans-complementation experiments with isomerase-defective mutants have shown that the catalytic activity of Cyclophilin A is not required for its function during HIV-1 uncoating (Saphire et al., 2002).

Instead, a recent report has suggested that Cyclophilin A may actually be present in the HIV-1 core to counteract the inhibitory effects of Ref-1 in human cells and promote the inhibitory effects of Lv-1 in simian cells (Towers et al., 2003). Specifically, it was found that by mutating the Cyclophilin A binding site in CA or by treating target simian cells with Cyclosporin A, Lv-1 restriction of HIV-1 infection was abrogated. Conversely, similar experiments in human cells caused an enhancement of Ref-1 mediated restriction of HIV-1 infection. Thus, it was suggested that Cyclophilin A may in this way modulate the host species specificity of HIV-1, ensuring that it can replicate efficiently only in the host it has evolved to infect (humans) and not in unnatural hosts such as the non-human primates. It is particularly interesting that in addition to evolving its own mechanisms of fighting cellular restrictions (i.e., Vif-mediated abrogation of APOBEC3G activity), in using Cyclophilin A to combat Lv-1 and Ref-1 restrictions, HIV-1 has also evolved an approach to use the cell against itself. However, the basic biochemical mechanisms of Lv-1 and Ref-1 restrictions await elucidation. As more is learned about these restriction mechanisms, not only will we better understand the process of retroviral uncoating, but simian models for AIDS pathogenesis studies may prove possible. Furthermore, it may even be possible to create synthetic Lv-1 mimics for the purpose of anti-HIV therapy.

To be able to begin addressing questions about retroviral uncoating, it is first necessary to understand how retroviruses enter cells. Since virus entry and fusion precede uncoating, it is reasonable to assume that information learned about the cell biology of these early processes could provide opportunities to investigate uncoating. Thus, I chose to study the cell biology of retroviral entry using a simple model system, the avian sarcoma and leukosis viruses.

The Avian Sarcoma and Leukosis Viruses

Figure 9:
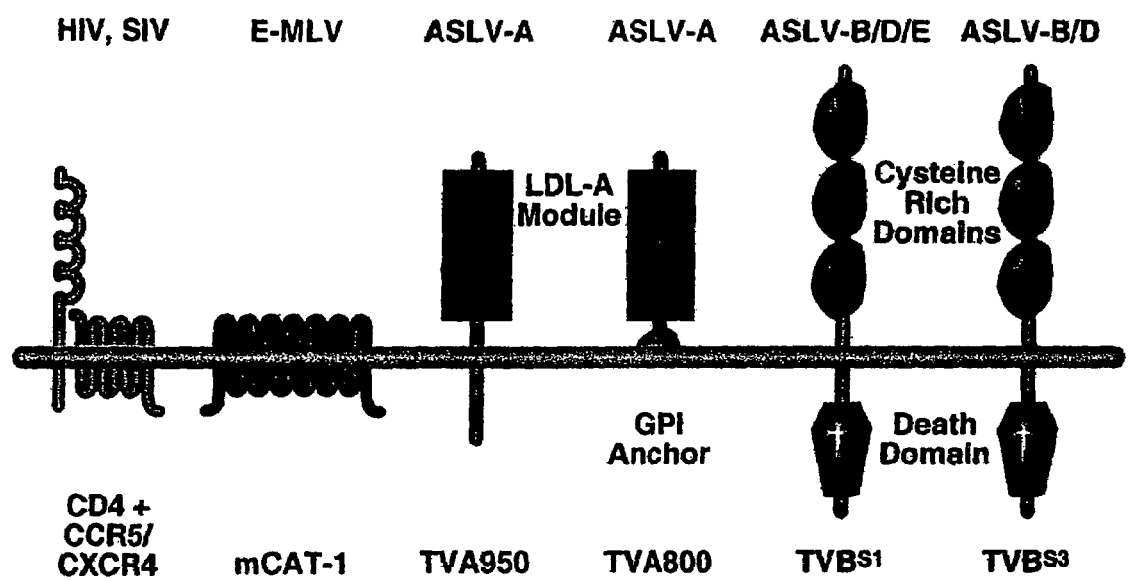
FIG. 9. Cellular receptors for the Avian Sarcoma and Leukosis Viruses (ASLV). Most retroviruses use either multiple-membrane spanning proteins (the ecotropic murine leukemia virus (E-MLV) uses a cationic amino acid transporter mCAT-1) or bi-partite receptor systems (HIV-1 uses the CD4 molecule as a receptor and the CCR5 or CXCR4 molecule as a co-receptor). However, the ASLV receptors cloned thus far are simple, single transmembrane proteins, simplifying analysis of Env-receptor interactions. The cellular receptors for subgroups A, B, D, and E ASLV are now known. TVA950 and TVA800 are expressed from alternatively spliced mRNAs, and both proteins function as a receptor for ASLV-A. Both TVA proteins contain the same extracellular N-terminal Env-binding domain, which contains a single copy of the low-density lipoprotein-A (LDL-A) module, the ligand-binding domain found in multiple copies within the LDL receptor. However, TVA950 is a transmembrane protein with a short cytoplasmic tail, while TVA800 lacks a transmembrane domain and is instead GPI-anchored. The $TVB^{S1}$ and $TVB^{S3}$ proteins function as cellular receptors for ASLV-B, -D, and -E or ASLV-B and -D, respectively. Both $TVB^{S1}$ and $TVB^{S3}$ are transmembrane proteins containing three cysteine-rich regions within their extracellular domains and death domains within their cytoplasmic tails. The sequences of these two proteins are identical except at a single residue in the second cysteine-rich domain of $TVB^{S1}$ (Ser-62 to Cys).

The avian sarcoma and leukosis viruses (ASLV) consist of a family of simple, chicken retroviruses that provide an attractive model system for addressing questions about the basic mechanisms of retroviral entry. The ASLVs have been divide into ten subgroups (A-J) based on studies examining receptor specificity, neutralizing-antibodies, and cross-interference of infection (Weiss, 1993). The cellular receptors for subgroups A, B, D, and E ASLV have been cloned (FIG. 9). Unlike most retroviruses that use either multiple-membrane spanning proteins or bi-partite receptor systems (i.e., receptor and co-receptor), the ASLV receptors are simple, single transmembrane proteins, thus simplifying analysis of Env-receptor interactions. Furthermore, while the envelope proteins of viruses in the different ASLV subgroups are remarkably similar, the corresponding cellular receptors differ dramatically (see below). Thus, this family of viruses has provided an ideal system to identify conserved mechanisms of Env-receptor interactions. Such studies have suggested that ASLV uses a novel, two step mechanism to enter cells. This mechanism, termed 'receptor-priming', involves activation of the fusogenic potential of Env via both receptor interactions and low pH (for a recent comprehensive review see (Barnard et al., 2003)).

The ASLV Envelope Protein. Like other retroviral envelope proteins, ASLV Env is expressed as a precursor polyprotein that assembles as a homotrimer and is proteolytically processed into the SU and TM subunits that remain linked via a disulfide bond. The TM subunit contains the fusion peptide and two heptad repeat domains required for fusion, as well as a membrane-spanning domain anchoring Env in the viral membrane. The SU subunit contains receptor-binding determinants. Specifically, there are five regions of variable amino acid sequence within SU that seem to determine receptor choice and thus, host range specificity of the different ASLV subgroups. These consist of two large regions (host range or hr1 and hr2) and three smaller variable regions (vr1, vr2, and vr3). Of these regions, it seems that hr1 and hr2 play the most important role in receptor usage (Barnard et al., 2003). This idea is supported by evidence from a variety of different mutational studies. For example, subgroup B ASLV (ASLV-B) viruses selected to be able to infect cells expressing the receptor for ASLV-E had alterations in the hr1 region of SU, which allowed the virus to utilize both ASLV-B and ASLV-E receptors (Taplitz et al., 1997). Such host range extension mutants have been observed for other subgroups of ASLV as well. In addition, evidence supports the notion that the vr3 region also participates in determining host range, albeit in a secondary role to the hr1 and hr2 regions. The functions of vr1 and vr2 remain unknown.

Since hr1, hr2, and vr3 are in separated regions of SU, it has been proposed that these regions may come together in the context of the folded envelope protein to form a receptor-binding site (Barnard et al., 2003). In support of this hypothesis, certain residues of ASLV-B hr1 and hr2 can be chemically cross-linked to a 15-amino acid peptide that has been shown to function as a minimal soluble receptor for ASLV-B virus particles (see below). A complete understanding of Env-receptor interactions awaits high-resolution crystal structures of the ASLV viral envelope glycoproteins bound to their cognate receptors.

Cellular Receptors for Subgroups A, B, D, and E ASLV. The ASLV-A receptor was cloned by a gene transfer approach using a retroviral vector-based exon-trapping strategy and mapped to the chicken tumor virus A (tva) gene (Bates et al., 1993; Young et al., 1993). Two splice-variants of the tva-encoded mRNA (designated as TVA950 and TVA800) were identified that confer susceptibility to ASLV-A infection when introduced into mammalian cells that are normally resistant to infection. Both TVA proteins contain the same extracellular N-terminal domain. However, TVA950 is a type I transmembrane protein with a short C-terminal cytoplasmic tail, while TVA800 lacks a transmembrane domain and is instead GPI-anchored (FIG. 9). Biochemical studies have shown that ASLV-A Env (EnvA) specifically binds the extracellular domain of TVA with high affinity ($K_D$=0.3 nM) (Connolly et al., 1994; Gilbert et al., 1994; Zingler et al., 1996). The extracellular domain of TVA contains a single copy of the LDL-A module, the ligand-binding domain found in multiple copies within the LDL receptor, and intramolecular disulfide bonds as well as coordination of a single calcium ion have been shown to be important for the correct folding of the TVA LDL-A module (Belanger et al., 1995; Wang et al., 2002). Currently, the natural ligand and function of TVA remain unknown, and due to technical difficulties, it remains unclear which TVA isoform is the naturally occurring receptor for ASLV-A in chicken cells.

The cellular receptors for ASLV-B, -D, and -E are encoded by alleles of the tvb gene. The tvb$^{S3}$ allele encodes a receptor for ASLV-B and -D, and is believed to be the chicken homolog of the human tumor necrosis factor receptor (TNFR)-related death receptors (TNFR apoptosis-inducing ligand [TRAIL] receptors) TRAIL-R1 and TRAIL-R2 (Brojatsch et al., 1996; Smith et al., 1998). TVB$^{S3}$ is a type I membrane protein containing three cysteine-rich domains within its extracellular domain and a death domain within its cytoplasmic tail (FIG. 9). Interestingly, during the acute phase, ASLV-B or -D infections kill up to 40% of the cells in culture (Weller et al., 1981), and it has been proposed that these cytopathic effects may be exerted via the death domain of the TVB$^{S3}$ receptor (Brojatsch et al., 1996). The tvb$^{S1}$ allele encodes a protein that is identical to TVB$^{S3}$ except at a single residue in the second cysteine-rich domain (Ser-62 to Cys) (FIG. 9) (Adkins et al., 2000). However, TVB$^{S1}$ functions as a receptor for ASLV-B, -D, and -E, and this difference in receptor function between TVB$^{S1}$ and TVB$^{S3}$ correlates with the formation of different disulfide bonds in the extracellular domain due to the presence of Cys-62 (Adkins et al., 2000). Finally, it was recently shown that a 15-amino acid linear peptide derived from the N-terminus of TVB$^{S1}$ functions as a minimal, soluble receptor for ASLV-B, allowing viral entry into receptor-negative cells (Knauss et al., 2002). The mechanism of action of this minimal receptor remains unknown.

A model has been proposed for how ASLV receptors may interact with their cognate envelope proteins. This model suggests that the receptor-binding domain formed by the hr1 and hr2 regions of SU may specifically recognize a large, hydrophobic residue exposed on the surface of the receptor. Mutational analysis of Trp-48 in TVA and Tyr-42 in TVB support this hypothesis, and this may be a general mechanism for retroviral Env-receptor interactions since similarly important hydrophobic residues in the HIV receptor CD4 and the MLV receptor mCAT1 have been found (Barnard et al., 2003).

Figure 10:
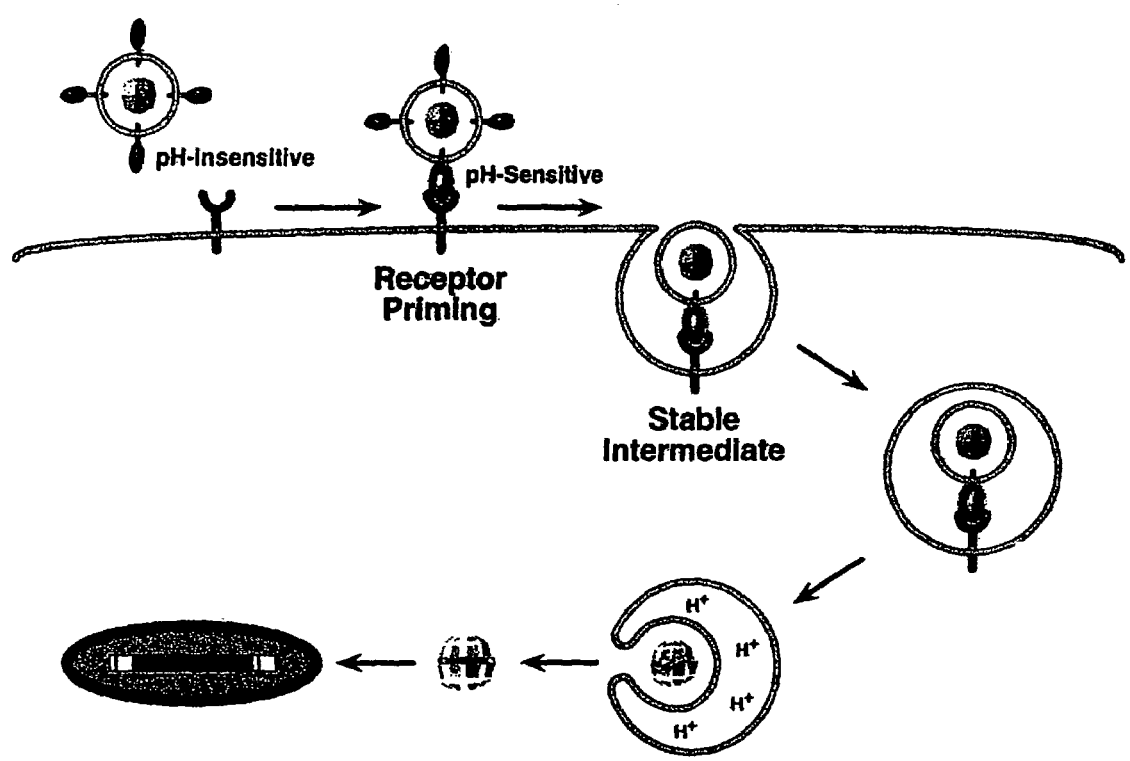
FIG. 10. Model for receptor-primed, low pH dependent entry of ASLV. Recent studies with ASLV have provided evidence for a third novel mechanism of activating viral envelope proteins: ASLV Env is activated via a combination of receptor-interaction and low pH. Specifically, this model proposes that upon binding its receptor, ASLV Env undergoes a first set of conformational changes termed receptor 'priming'. This priming reaction converts Env from being insensitive to low pH to being able to undergo a second set of conformational changes when exposed to low pH. The viral receptor-primed intermediate remains stable in cells until exposure to acid pH. Ultimately, these conformational changes together are predicted to result in membrane fusion out of acidic endosomes.

Receptor Primed, Low pH Activation of ASLV Env: a Novel Mechanism of Viral Entry. As discussed above, it is believed that either interactions with a receptor or the low pH within endosomes activates the fusogenic potential of viral Env proteins. However, recent studies with ASLV have provided evidence for a third novel mechanism of activating viral envelope proteins: ASLV Env is activated via a combination of receptor-interaction and low pH (Barnard et al., 2003; Mothes et al., 2000). Specifically, this model suggests that ASLV Env, upon binding its receptor, undergoes a first set of conformational changes termed receptor 'priming'. This priming reaction converts ASLV Env from being insensitive to low pH to being able to undergo a second set of conformational changes when exposed to low pH. Receptor priming may be sufficient to allow lipid mixing between viral and cellular membranes (Earp et al., 2003). However, delivery of the viral core into the cytoplasm does not occur until exposure of Env to low pH (Barnard et al., 2003). It is predicted that these conformational changes together result in membrane fusion, presumably out of acidic endosomes (FIG. 10).

Different lines of evidence support the receptor-priming model for ASLV entry. That low pH is required during entry was shown by the observation that lysosomotropic agents such as $NH_4Cl$, which neutralize the pH within acidic intracellular compartments, block ASLV entry. This block was abrogated by replacing the envelope on ASLV particles with that of MLV, a low pH-independent virus, indicating that the low pH requirement maps solely to Env-mediated fusion. Importantly, using various biochemical assays that directly examine the fusion activation state of Env, it was shown that ASLV Env was triggered by low pH, but only after exposure to receptor (Mothes et al., 2000).

The receptor-priming model predicts that upon binding its receptor, ASLV enters the cell by endocytosis. Consistent with this, expression of dominant negative dynamin-1 inhibited ASLV entry into cells (Mothes et al., 2000).

The invention will be further described by the following non-limiting examples.

EXAMPLE I

The two-step model for ASLV entry predicts that following receptor binding and priming, virions are taken up into cells by endocytosis and then trafficked to an acidic endosomal compartment where fusion occurs (fusion compartment). Consistent with this notion, ASLV entry is blocked by expression of a dominant-negative dynamin-1 protein (Mothes et al., (2000)). To further explore this model of viral entry, we have now followed the fate of subgroup A ASLV (ASLV-A) virions that enter cells expressing either the transmembrane form or the glycophosphatidylinositol (GPI)-anchored form of TVA, the cellular receptor for ASLV-A (Bates et al., 1993; Young et al., 1993)). The data obtained indicate that virions are taken up into cells and are trafficked to and escape from putative acidic fusion compartments with different kinetics depending upon the type of TVA receptor used. When infection of cells that express the GPI-linked TVA protein was transiently blocked with $NH_4Cl$, virions remained highly infectious. However, the same treatment of cells that express the transmembrane TVA receptor led to a striking loss of viral infectivity. This difference in viral infectivity correlated with association of the GPI-linked TVA protein with detergent-resistant membranes (DRMs) and indicates that ASLV-A can be trafficked to different intracellular compartments depending upon the nature of the receptor used.

Materials and Methods

Chemicals and plasmid DNA. All chemicals were purchased from Sigma unless otherwise stated. Stock solutions of 500 mM $NH_4Cl$ and 100 mM methyl-β-cyclodextrin (MβCD) were made in water and stored at 4° C. and −20° C., respectively. Fumonisin B1 stock solutions (5 mg/ml in dimethyl sulfoxide) were made just prior to use. The plasmids pCMMP (murine leukemia virus [MLV] vector), pCMMP EGFP, pMD.old.gagpol (encoding MLV Gag and Gag-Pol proteins), and pMD.G (encoding the vesicular stomatitis virus G protein) have been described previously (Boerger et al., 1999; Ory et al., 1996)). The plasmid encoding Gαi-DsRed (Kaykas et al., 2001)) was a generous gift from Bill Sugden (McArdle Laboratory, University of Wisconsin).

Cell lines and viruses. Human 293 cells were transduced with retroviral vectors that encode TVA950 or TVA800 (Ory et al., 1996). Briefly, the genes encoding these forms of TVA were subcloned into the MLV vector pCMMP. The resulting plasmids (pCMMP-TVA950 and pCMMP-TVA800) were then used in a tripartite transfection system along with plasmid pMD.old.gagpol and plasmid pMD.G as described previously (Boerger et al., 1999). Virus-containing supernatants were then collected 48, 72, and 84 hours posttransfection, pooled, and stored at −80° C. after filter sterilization. These viruses were used to infect 293 cells, and expression of either TVA950 or TVA800 was subsequently confirmed 4 days later by flow cytometry using SUA-rIgG, a recombinant ASLV-A SU immunoglobulin G (rIgG) fusion protein, as described previously (Zingler et al., 1996). The fluorescence-activated cell sorter-analyzed 293 (TVA950) and 293 (TVA800) cells expressed equivalent levels of cell surface receptors as judged by SUA-rIgG binding (data not shown). The vector RCASBP (A)-EGFP was used to generate ASLV-A virus stocks (Snitkovsky et al., 2000; Snitkovsky et al., 2001).

Viral infections, citrate buffer, and $NH_4Cl$ treatments. For infections, cells were rinsed once with Hank's balanced salt solution (HBSS) (Gibco) and dislodged from the plate with HBSS containing 5 mM EDTA at 37° C. An equal volume of ice-cold medium was added, and the cells were harvested by centrifugation at 1,000×g for 5 minutes at 4° C. Cells were washed twice with ice-cold medium and then incubated with RCASBP(A)-EGFP at multiplicities of infection (MOIs) ranging from 0.8 to 2.8 enhanced green fluorescent protein (EGFP)-transducing units for 1 hour at 4° C. on a rocker (Nutator). Unbound virions were removed by rinsing with cold HBSS, and virus-cell complexes were transferred to ice-cold tissue culture plates. Infection was initiated (at a time designated as t=0) by shifting the cells to 37° C. In the citrate buffer inactivation experiments, $10^6$ virus-loaded cells were incubated at 37° C. for the indicated times, returned to ice, and harvested by centrifugation at 14,000×g for 1 minute at 4° C. The cell pellet was resuspended in 1 ml of citrate buffer (pH 3.0) (Kizhatil et al., 1997) and incubated for 2 minutes at room temperature to inactivate the surface-bound virions. The cells were then centrifuged at 14,000×g for 1 minute and washed twice with 1 ml of cold phosphate-buffered saline (PBS) (pH 7.4) and once with 1 ml of ice-cold medium. Cells were plated in a six-well tissue culture plate in 2 ml of medium and incubated at 37° C. for 48 to 72 hours. Samples were then analyzed by flow cytometry using a FACScalibur instrument (Becton Dickinson) to monitor EGFP expression in the infected cells (Snitkovsky et al., 2000). In the $NH_4Cl$ inhibition experiments, either $7.5×10^5$ cells/sample (for quantitative PCR [QPCR] analysis) or $4×10^5$ cells/sample (for EGFP analysis) were used to create virus-loaded cells as described above. The $NH_4Cl$ was added to medium at a final concentration of 30 mM at different time points and, where indicated, washed out by removing the medium and rinsing the cells with PBS (pH 7.4).

Quantification of viral entry by QPCR. The real-time QPCR experiments to detect early reverse transcription products were performed essentially as described previously (Mothes et al., 2000). Late viral DNA products were quantified by a similar approach using the following primers: 5'ACCACTGAATTCCGCATTGC3' (sense) (SEQ ID NO:1), 5'GGCCGACCACTATTCCCTAAC3' (antisense) (SEQ ID NO:2), and 5'CCCTGACGACTACGAGCACCTG-CAT3' (SEQ ID NO:3) (FAM Taqman probe; Perkin Elmer). A dilution series of RCASBP(A)-EGFP proviral DNA contained in a plasmid vector was used to construct a standard curve to quantify viral DNA. Routinely, between $10^2$ and $10^7$ DNA molecules were accurately measured by this assay.

MβCD and Fumonisin B1 treatments. In the experiments involving MβCD treatment, $3×10^6$ cells on 6 cm dishes were rinsed twice with serum-free medium (SFM) (prewarmed to 37° C.) and treated at 37° C. for 15 minutes with 2 ml of SFM containing 15 mM MβCD. The cells were then rinsed twice with prewarmed SFM, once with ice-cold SFM, and incubated at 4° C. for 1 hour with 2 ml of ice-cold SFM containing virus. Following removal of unbound virus with cold HBSS, cold medium was added and infection was initiated by shifting the cells to 37° C. NH$_4$Cl was added at the indicated times (i.e., t=0 and t=60 minutes) and 6 hours later washed out as described above. Samples were analyzed after about 100 hours by flow cytometry to monitor EGFP expression. In the Fumonisin B1 experiments, 10$^5$ cells in six-well tissue culture plates were incubated with 40 μg of Fumonisin B1-containing medium/ml for 60 hours. Virus infection, NH$_4$Cl treatment, and EGFP expression analysis were carried out as described above, except that these experiments were performed at an MOI of 0.16 EGFP-transducing units (determined without inhibitor).

Fractionation of detergent-soluble and -insoluble membranes. 293(TVA950) or 293(TVA800) cells plated at 20 to 40% confluency on a 10 cm tissue culture plate were transfected with plasmid DNA encoding the lipid raft marker Gαi-DsRed (Kaykas et al., 2001) by calcium phosphate precipitation. Forty-eight hours later, 10$^7$ cells were washed once with ice-cold PBS and then twice with 37° C.-prewarmed SFM. In MβCD extraction experiments, the cells were incubated for 15 minutes at 37° C. with medium containing 15 mM MβCD. The medium was then removed and cells were chilled on ice prior to 30 minutes of incubation at 4° C. with 2 ml of ice-cold lysis buffer (MBS buffer—25 mM morpholineethanesulfonic acid, 150 mM NaCl, pH 6.5, containing 0.5% Triton-X-100). The cell lysate was adjusted to 40% sucrose by addition of 2 ml of an 80% sucrose solution, and a 1-ml aliquot of this mixture was overlaid sequentially with 3.5 ml of 30% sucrose followed by 0.5 ml of 5% sucrose (all sucrose solutions were prepared in MBS). These samples were centrifuged at 240,000×g for 18 hours at 4° C. in a Beckman SW55Ti rotor. Twelve equal fractions were collected from the sucrose gradient and were mixed in a 1:1 ratio with 2×SDS sample buffer, boiled, and subjected to SDS-polyacrylamide gel electrophoresis. Gαi-DsRed and TVA proteins were detected by Western blotting using a horseradish peroxidase-coupled secondary antibody (Amersham Pharmacia) and either an anti-DsRed antibody (catalog numbers 8370 to 8372; Clontech) or SUA-rIgG (Zingler et al., 1996), respectively. TVA was quantitated in the different gradient fractions by quantitative Western blotting analysis using a $^{35}$S-labeled anti-rabbit antibody (catalog number SJ424-50; Amersham). The resultant blots were exposed to a phosphorimaging screen for 48 to 80 hours and analyzed using a Typhoon PhosphorImager and ImageQuant software (Molecular Dynamics).

Results

TVA800 is associated with DRMs, but TVA950 is not. Previously, two forms of the TVA receptor were identified: TVA950 is a transmembrane form, whereas TVA800 is a GPI-anchored protein (Bates et al., 1993; Young et al., 1993). To characterize the viral entry mechanisms associated with each of these receptors, it was determined if either one or both is associated with DRMs (or lipid rafts). Lipid rafts are believed to be microdomains of cellular membranes that are rich in cholesterol, sphingolipids, and GPI-linked proteins (Brown et al., 1998; Simons et al., 2000). Previous studies had indicated that the association of some viral receptors with lipid rafts was important for the efficiency of viral entry (for example, human immunodeficiency virus type 1 (Liao et al., 2001; Manes et al., 2000; Popik et al., 2002), ecotropic MLV (Lu et al., 2000), and simian virus 40 (Pelkmans et al., 2001; Pelkmans et al., 2002)).

Figure 11:
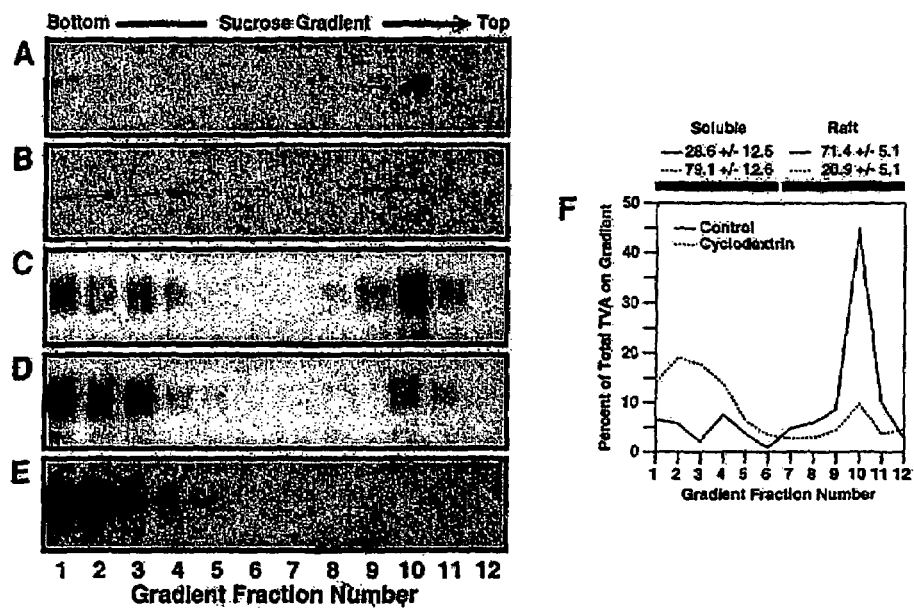
FIG. 11. TVA800 is associated with detergent resistant membranes (DRMs) but TVA950 is not. Transfected human 293 cells expressing the lipid raft marker Gαi-DsRed and either TVA800 or TVA950 were either left untreated (A, C, and E) or were treated for 15 minutes at 37° C. with 15 mM methyl-beta cyclodextrin (MβCD) prior to ice-cold Triton X-100 lysis and sucrose gradient sedimentation (B and D).

To test DRM association, TVA800- and TVA950-expressing cells were lysed in a Triton X-100-containing buffer at 4° C. and subjected to flotation analysis by using a sucrose step gradient. Under these conditions, DRMs float toward the top of the gradient, whereas detergent-soluble fractions remain at the bottom (Chamberlain et al., 2001; Fra et al., 1994). Greater than 70% of the total TVA800 cofractionated with Gαi-DsRed, a coexpressed DRM-associated marker protein (FIGS. 11A and C, fractions 9 to 11, and F). Moreover, like the marker protein, most of the TVA800 was solubilized when cells were treated with MβCD to disrupt DRMs by cholesterol extraction (FIGS. 11B and D, fractions 1 to 4, and F). These data demonstrated that a substantial portion of TVA800 was associated with DRMs. By contrast, the TVA950 protein was found exclusively in the detergent-soluble fraction of cell membranes (FIG. 11E, lanes 1 to 4), and disruption of DRMs had no effect on the localization of TVA950 (data not shown). Therefore, the two TVA receptors seem to exist in different microdomains of cellular membranes.

TVA950 promotes faster virus uptake than does TVA800. Recently, several lipid raft-dependent endocytic pathways have been described that are distinct from classical clathrin-mediated endocytosis (Ikonen, 2001; Nichols et al., 2001). Thus, the DRM association of TVA800 but not TVA950 suggested that the viral entry properties associated with each of these receptors might be distinct. To explore this possibility, the rates of virus internalization in cells that express equivalent cell surface levels of TVA950 or TVA800 was determined. ASLV-A virions encoding the EGFP were bound to cells at 4° C. and then infection was initiated by shifting the temperature to 37° C. At different time points thereafter, residual surface-associated virions were inactivated by addition of a pH 3.0 citrate-containing buffer (Kizhatil et al., 1997). The efficiency of subsequent viral infection was then determined using flow cytometric analysis to measure the proportion of EGFP-expressing cells. Under the conditions used, citrate buffer treatment inactivated approximately 80% of cell surface-associated virions (FIG. 12A, t=0).

TVA950 mediated rapid virus uptake, reaching a maximal level only 5 minutes after initiating infection (FIG. 12A). By contrast, TVA800-dependent viral entry displayed slower kinetics, with only approximately 50% of the total virions internalized after 5 minutes and the remainder being internalized more slowly up to 15 minutes later (FIG. 12A.). These data demonstrated that the rate of virion uptake was dependent upon the type of TVA receptor used.

Virions from the cell surface reach and exit a putative acidic endosomal fusion compartment with similar kinetics when entering via either TVA receptor. To determine how quickly virions bound to TVA950 or TVA800 at the cell surface are trafficked to and escape from a putative acidic endosomal fusion compartment(s), the time required for these viruses to become resistant to inhibition by NH$_4$Cl was determined. NH$_4$Cl is a lysosomotropic agent that causes a rapid elevation in endosomal pH, thus blocking low-pH-dependent cellular processes (Okuhuma et al., 1981; Okhuma et al., 1978). A 10 hour treatment of cells with 30 mM NH$_4$Cl was initiated at different time points after beginning infection, and subsequent viral infection was quantified using a real-time PCR assay for reverse-transcribed DNA (QPCR). These studies showed that when NH$_4$Cl was added at the time of initiating infection or 10 minutes later, there was a complete block to infection of both cell types (FIG. 12B). By contrast, NH$_4$Cl addition at 20 minutes or later after initiating infection had a greatly reduced effect upon viral infectivity (FIG. 12B). Presumably at these later time points a fraction of the virus had proceeded beyond the low-pH-sensitive step of infection.

By subjecting these data to linear regression analysis, it was determined that virus became resistant to $NH_4Cl$ treatment with a half time of 23 or 22 minutes when entering via TVA950 or TVA800, respectively (FIG. 12B). Interestingly, infection of both cell types resumed immediately after $NH_4Cl$ withdrawal (FIG. 12C), indicating that virions may have fused upon reacidification of the endosomal compartment in which they were presumably trapped during the period of inhibitor treatment. Taken together, the data in FIG. 12 suggest that virus bound to TVA800 is taken up from the cell surface more slowly than that bound to TVA950, but the TVA800-associated particles are delivered to a putative acidic endosomal fusion compartment more quickly than those associated with TVA950.

$NH_4Cl$-arrested virions in TVA800-expressing cells remain highly infectious, whereas those in TVA950-expressing cells do not. When following the fate of virions after $NH_4Cl$ withdrawal by QPCR analysis of viral DNA products, a striking difference was seen in the residual level of viral infectivity between cells expressing either TVA800 or TVA950 (FIG. 13A). Viral infection was completely arrested in both cell types during the 6 hour period of inhibitor treatment (FIG. 13A). However, upon $NH_4Cl$ release, the level of subsequent infection seen with TVA800-expressing cells was approximately 60% of that seen with an untreated cell population (FIG. 13A). By contrast, the number of viral DNA products generated in the TVA950-expressing cell population was only 10% of that seen with untreated cells (FIG. 13A). These data indicated that $NH_4Cl$-arrested virions remain highly infectious in TVA800-expressing cells but not in TVA950-expressing cells.

The previous experiment monitored viral infectivity by measuring the quantity of viral DNA products produced in the infected cell population. However, only 20% of the viral DNA made after infection remains stably integrated as proviral DNA in these cells (data not shown). Therefore, to monitor the fate of the infectious virions (i.e., those that go on to establish proviral DNA), a similar experiment was performed as that shown in FIG. 13A except that the expression of the virus-encoded EGFP was assessed as a measure of infectivity. The results obtained were strikingly similar to those obtained by the quantitative reverse transcription assay. Specifically, the efficiency of infection obtained with $NH_4Cl$-treated cells expressing either TVA800 or TVA950 was 85 and 20%, respectively, of that seen with untreated cells (FIG. 13B). Increasing the time of $NH_4Cl$ treatment to 12 hours caused a further decrease in infectivity of virions entering via TVA950 but did not affect those entering via TVA800 (data not shown). Together, these results demonstrated that $NH_4Cl$-arrested virions are much more stable in cells that express TVA800 as opposed to TVA950.

Disruption of DRMs markedly alters the stability of $NH_4Cl$-arrested virions in cells that express TVA800. To test whether TVA800 association with DRMs is responsible for the increased relative stability of $NH_4Cl$-arrested virions, cells expressing this receptor were treated with either MβCD or Fumonisin B1 (a sphingolipid biosynthesis inhibitor that also disrupts DRMs) (Chatterjee et al., 2001). Cyclodextrin treatment by itself had only a minor effect on viral infectivity regardless of which TVA receptor was used for entry (FIGS. 14A and C). However, when combined with a 6 hour $NH_4Cl$ block imposed at the time of initiating infection, this treatment led to a 50% loss of infectivity for virus entering via TVA800 (compare FIGS. 14A and 13B). This loss of viral infectivity was largely overcome when $NH_4Cl$ was instead added 60 minutes after initiating infection (FIG. 14A), a time when presumably a substantial fraction of virions had bypassed the low-pH-sensitive step (FIG. 12B). Similar results were obtained when cells were treated with Fumonisin B1 (FIG. 14B). To ensure that this cyclodextrin effect was specific for cells expressing the GPI-linked receptor, the same experiment was performed with TVA950-expressing cells. In this case, the $NH_4Cl$ treatment led to the same (approximately 80%) decrease in viral infectivity irrespective of whether cyclodextrin had been added or not (compare FIG. 14B with 13B). Thus, the reduced level of viral infectivity that was seen by combining ammonium chloride and cyclodextrin treatments was specific for the TVA800-expressing cells. Together, these data indicate that the increased stability of $NH_4Cl$-arrested virions in TVA800-expressing cells, relative to that seen with TVA950-expressing cells, closely correlates with the association of the GPI-linked receptor with DRMs.

Discussion

Previously, a model was proposed in which ASLV enters cells by receptor-mediated endocytosis followed by low-pH-dependent fusion from an intracellular compartment (Mothes et al., 2000). The present study provides evidence that ASLV-A virions associated with a transmembrane form of the TVA receptor are internalized more rapidly than those using a GPI-anchored form of the receptor. However, virions become resistant to inhibition by the lysosomotropic agent $NH_4Cl$ at similar rates regardless of which TVA receptor is used to enter the cells. Since these $NH_4Cl$ experiments measure the combined kinetics of the initial uptake and the subsequent trafficking of virus particles, the simplest model to explain these data would be that upon being internalized, virions associated with the GPI-anchored receptor are subsequently trafficked to a putative fusion compartment more rapidly than those using the transmembrane-anchored form.

Remarkably, most virions that entered cells expressing TVA800 remained highly infectious in the presence of $NH_4Cl$, whereas those entering TVA950-expressing cells did not. This difference between the two types of TVA receptors correlated with the lipid raft association of the majority of the TVA800 protein. These data suggest that association of the receptor with lipid rafts influences the intracellular fate of virions (FIG. 15). The simplest model to explain these findings is that virions entering via TVA950 are trafficked via a degradative endocytic pathway that may involve multivesicular bodies, late endosomes, and lysosomes (Gruenberg, 2001; Mukherjee et al., 1997). In contrast, virions entering cells via lipid raft-associated TVA800 may be endocytosed by a known, or as-yet-unknown, lipid raft-dependent endocytic pathway to a stable compartment. The loss of viral infectivity that was seen with $NH_4Cl$-treated TVA800-expressing cells (FIG. 13) may be due either to some intrinsic property of this "stable" compartment or, instead, might be due to virion uptake by receptors that reside outside of lipid rafts, which perhaps traffic the virus to a degradative compartment similar to that accessed by TVA950.

Consistent with this model, lipid raft-associated components seem to avoid the degradative endocytic pathway by being sorted into the recycling endosome, which contains a low level of endocytic proteases (Gagescu et al., 2000). Furthermore, some GPI-anchored proteins, such as folate receptor and CD55, are endocytosed and trafficked through this recycling endosome (Chatterjee et al., 2001; Mayor et al., 1998; Sabharanjak et al., 2002). Alternatively, TVA800-associated virions may use another lipid raft-dependent endocytic pathway, such as that used by CD59, which traffics directly between the plasma membrane and the Golgi apparatus (Nichols et al., 2001); that used by simian virus 40, a nonenveloped virus which enters cells via caveolae and accesses the endoplasmic reticulum via the caveosome, a novel sorting organelle (Pelkmans et al., 2001; Pelkmans et al., 2002); or that used by the interleukin-2 receptor, which seems to be independent of these other endocytic pathways (Lamaze et al., 2001). It is also possible that in the presence of $NH_4Cl$, virions bound to TVA800 and TVA950 are trafficked to different "domains" of the same intracellular compartment. In support of this idea, it was recently suggested that proteins targeted for degradation may be localized to the internal invaginations of late endosomes, while those found at the outer limiting membrane are poorly degradable (Gruenberg et al., 2001). The use of pathway-specific inhibitors as well as quantitative imaging techniques to track individual virions may help distinguish between these various models of viral entry.

By characterizing the entry pathway used by ASLV-A, better understanding of the mechanism by which this retrovirus enters cells is gained as well as new insights into how lipid raft-associated cargo is taken up into cells and delivered to an acidic endosomal compartment. To date, there has not been much information available on how such cargo is trafficked to an acidic endosome. This information, in turn, may help us better understand the entry mechanisms of other viruses that use GPI-anchored receptors, such as Jaagsiekte sheep retrovirus (Rai et al., 2001) and perhaps Ebola virus (Chan et al., 2001). In addition, the fact that ASLV-A infection can be arrested in TVA800-expressing cells by using $NH_4Cl$ is a novel finding, since low-pH-dependent viruses are generally unstable under these conditions, presumably because they have been delivered to a degradative compartment (Marsh et al., 1989). This feature of the ASLV system may allow for the isolation of virus-containing endosomes which, upon reacidification, may support virus-cell membrane fusion. If so, this system could allow for a detailed biochemical analysis of receptor priming, fusion, and of viral uncoating that leads to reverse transcription.

EXAMPLE II

The first steps of retroviral infection involve virus interaction with specific cell surface receptors followed by the fusion of viral and cell membranes, delivering the viral ribonucleoprotein core particle into the cytoplasm (Eckert et al., 2001; Barnard et al., 2003; Pierson et al, 2002). The viral core particle is then presumed to undergo an uncoating step leading to the activation of reverse transcription within a reverse transcription complex (RTC) (Dvorin et al., 2003; Goff, 2001).

It has been hypothesized that cellular factors may be involved in the earliest steps of retroviral uncoating (Goff, 2001). Indeed, in the case of HIV-1, the cellular protein cyclophilin A appears to be important (Braaten et al., 1996). Cyclophilin A is incorporated into assembling virions by virtue of binding the capsid (CA) domain of the viral Gag polyprotein (Franke et al., 1994; Luban et al., 1993; Thali et al., 1994). Cyclosporin A, an immunosuppressant that disrupts the CA-cyclophilin A interaction, inhibits HIV-1 infection at a step before the initiation of reverse transcription (Braaten et al., 1996; Thali et al., 1994; Karpas et al., 1992). Although cyclophilin A is a peptidyl-prolyl cis-trans isomerase, its enzymatic activity is not required for its function during HIV-1 uncoating (Saphire et al., 2002). Instead, cyclophilin A seems to counteract the inhibitory effects of Ref-1, a restriction factor(s) expressed in human cells that would otherwise interfere with the onset of reverse transcription (Towers et al., 2003).

In addition to cellular factors that are assembled into virions, those present in the target cell may also influence the earliest events in retroviral uncoating (Goff, 2001). In support of this hypothesis, a mutant cell line has been isolated that supports virus-cell membrane fusion but not reverse transcription (Gao et al., 1999). In addition, certain simian cell lines exhibit a partial, innate resistance to this step of HIV-1 infection (Munk et al., 2002; Bieniasz, 2003). This phenomenon, termed Lv-1 restriction, is analogous to Ref-1 restriction in human cells (Bieniasz, 2003; Towers et al., 2003). In certain primates, Lv-1 restriction is modulated by cyclophilin A present in the HIV-1 particle (Towers et al., 2003). Recently, TRIM -5α was identified as a candidate component of Lv-1 restriction (Stremlau et al., 2004).

Although cellular factors have been implicated in retroviral uncoating, their role and the precise events surrounding the formation of the RTC remain poorly understood. A major hurdle in efforts to understand these processes has been the lack of a cell-free system that reproduces retroviral fusion, uncoating, and the initiation of reverse transcription in vitro. To establish a system to analyze uncoating events, the entry mechanisms of a model retrovirus, ASLV, were investigated. The studies presented here suggest that ASLV uses a novel entry mechanism, termed the 'receptor priming' model, in which receptor interaction followed by exposure to acid pH activates ASLV fusion. Subgroup A ASLV (ASLV-A) entering cells via a GPI-anchored form of the cellular receptor (TVA800) is shown to use a novel clathrin-mediated endocytic pathway in which clustering of receptors in lipid rafts functions to specify target virus particles to an acidic compartment, thereby directly confirming predictions made by the receptor-priming model. However, unlike most other low pH-dependent viruses, which are rapidly degraded under fusion-arrested conditions, ASLV-A can remain highly infectious within the fusion compartment when infection is transiently arrested prior to fusion. The development of such a system, which derives from the remarkable stability of avian sarcoma and leukosis virus (ASLV) particles when viral penetration into the cytosol is blocked by treatment with lysosomotropic agents that elevate endosomal pH (Melikyan et al., 2004; Mothes et al., 2000; Narayan et al., 2003; Smith et al., 2004), is described below.

In this system, fusion-arrested virions are induced to fuse out of endosomes in vitro allowing the released core to uncoat and reverse transcribe in the test tube. The block to viral replication is removed by inhibitor withdrawal, and the viral cores are released into solution, where they are amenable to biochemical manipulation. This system was used to obtain direct evidence that a cellular factor(s) as well as ATP hydrolysis promote early ASLV DNA synthesis and that a nuclear factor(s) stimulates viral late DNA synthesis. This assay was also adapted to reconstitute uncoating of the human immunodeficiency virus (HIV-1). It is shown that ATP hydrolysis and cellular factors greater than 5 kDa in size are required for both HIV and ASLV uncoating in vitro. The cell-free system was also used to reconstitute restrictions by Ref-1 and Lv-1, naturally occurring cellular inhibitors of HIV-1 uncoating. The cell-free system, which reconstitutes retroviral fusion and uncoating, provides a tool to define uncoating mechanisms of HIV-1 and other retroviruses, the mechanisms of restriction factors, and to facilitate the identification and characterization of the cellular factors involved in each process.

Materials and Methods

Cells, Viruses, and Materials. All chemicals were from Sigma unless otherwise stated. Stock solutions of 25 mM MgCl$_2$, 10 mM d NTPs (Stratagene), and 500 mM NH$_4$Cl were made and stored at 4° C., −20° C., or prepared fresh for every experiment, respectively. Homogenization buffer (HB, 250 mM sucrose/3 mM imidazole, pH 7.4) was stored at 4° C., and 1× protease inhibitor mixture (Roche Diagnostics) was added just before each use. The construction of human 293(TVA800) cells has been described (Narayan et al., 2003). The subgroup A-specific ASLV vector RCASBP(A)-EGFP virus, encoding the enhanced green fluorescent protein (EGFP), was harvested from extracellular supernatants of chronically infected DF-1 cells (Snitkovsky et al., 2000; Snitkovsky et al., 2001).

The HIV [EnvA] pseudotyped virus was generated in the extracellular supernatant of approximately 5×10$^6$ cells human 293 cells transiently transfected using lipofectamine 2000 (Invitrogen) with 2.5 µg of plasmid pR9ΔEnv (Zhou and Aiken, 2001), 2.5 µg of plasmid pMM310 (both kindly provided by M. Miller [Merck] and also see Munk et al. (2002)), 3 µg of plasmid pCB6 envAΔ513 (kindly provided by B. Lewis (Memorial-Sloan Kettering), see Lewis et al. (2001)), and 2 µg of plasmid pDK3 dsRed (for transfection efficiency) (Knauss and Young, 2002). The virus-containing supernatants were collected 24, 48, and 72 hours later, pooled and centrifuged at 3000×g for 10 minutes and then passed through a 0.45 µm filter. The filtered viral supernatants were treated with DNase I (40 units/ml) for 1 hour at room temperature to remove contaminating plasmid DNA prior to storage at −80° C. Alternatively, the virus was concentrated approximately 15-fold by centrifugation over a 5 ml sucrose cushion (15% w/v sucrose in MH buffer-25 mM MES, 25 mM HEPES pH 7.4) at 100,000×g for 1 hour at 4° C. (Snitkovsky et al., 2000; Snitkovsky et al., 2001).

Cell-Free Fusion and Uncoating Reactions. 293(TVA800) cells were challenged with the RCASBP(A)-EGFP vector at the indicated multiplicities of infection (MOIs) in the presence of 30 mM NH$_4$Cl (Narayan et al., 2003). Infection was initiated for 6 hours by a temperature shift from 4° C. to 37° C. The cells were then dislodged from the plate by repeated pipetting and centrifuged at 1,000×g for 5 minutes at 4° C. Approaches previously used to establish cell-free systems for endosome-endosome fusion (Gruenberg et al., 1989; Gorvel et al., 1991; Robinson et al., 1998) were adapted to establish the virus fusion/uncoating assay. Specifically, the cell pellet was resuspended at a concentration of 1.67×10$^7$ cells per ml in HB containing 30 mM NH$_4$Cl at 4° C. Approximately 1.25×10$^7$ cells were then passed eight times through a pre-chilled ball-bearing cell cracker (10 µm clearance, European Molecular Biology Laboratory; see Gorvel et al. (1991) and Robinson et al. (1998)) by using 1-ml syringes. These conditions routinely allowed for >80% of the cells being broken with minimal nuclear lysis as judged by light microscopy (Robinson et al., 1998). The cell lysate was then subjected to centrifugation at 1,000×g for 10 minutes at 4° C. to pellet unbroken cells and nuclei and generate the viral postnuclear supernatant (VPNS). Endosomal latency in these preparations was measured at about 70% by using horseradish peroxidase as an endosomal marker (Robinson et al., 1998).

The standard fusion/uncoating reaction consisted of 30 µl of freshly prepared VPNS (i.e., from 5×10$^5$ cells) in a total volume of 300 µl of HB+/−(3 mM MgCl$_2$/50 µM dNTPs/60 mM NH$_4$Cl/100-200 µg of S10 fraction representing the supernatant from a 1,000×g and then 10,000×g spin of a lysate prepared in HB from uninfected 293 cells by Dounce homogenization). As indicated, in some reactions the 293 S10 fraction was substituted with a yeast cell S10 extract (Ausubel et al., 2000). Alternatively, reactions were set up with the 293 S10 fraction or with an equivalent amount of 293 S10 fraction that had either been subjected to gel filtration over a PD-10 desalting column (M$_r$>5,000) (Amersham Pharmacia), to dialysis against HB using a Slide-A-Lyzer (3.5-kDa membrane cutoff) (Pierce), or to membrane filtration (5-kDa membrane cutoff) (Vivaspin). In some reactions, the 293 S10 fraction was substituted with the same cell equivalent amounts of either a P100 or S100 cell fraction representing the pellet and supernatant, respectively, of a 100,000×g spin of the 293 cell homogenate. In others, 20 µM cyclosporin A, 2.5 or 4.5 mM adenosine 5'-[γ-thio]triphosphate or 10 units/ml apyrase was added either before initiating the reaction or at the indicated times after shifting to 37° C., respectively. Aliquots of S10 fractions from CV-1 or FrHL-2 cells were also added where needed.

A similar protocol was used when examining late DNA products of ASLV reverse transcription with the exception that the 293 (TVA800) cells were challenged with the RCASBP(A)-EGFP vector at MOIs of about 1.0 EGFP-transducing unit. Standard fusion/uncoating reactions were set up as described above either with or without an aliquot of a nuclear extract (representing that derived from 1.6×10$^6$ 293 cells prepared as described in Farrell et al., 2002) added before initiating infection by temperature shift.

All reactions were performed at 37° C. for 6-12 hours unless otherwise stated, and stopped by a 15 minute incubation with 100 µg of Proteinase K (Boehringer Mannheim) at room temperature before shifting samples to −80° C. The DNA contained in these samples was purified by using phenol/chloroform/isoamylalcohol extraction (Ausubel et al., 2000) and the precipitated DNA was resuspended in 50 µl of distilled water and stored at −20° C. (Mothes et al., 2000; Narayan et al., 2003). Both early and late DNA products of ASLV reverse transcription were measured by a quantitative real-time PCR amplification method as described (Mothes et al., 2000; Narayan et al., 2003).

Results

A Cell-Free System That Reconstitutes Retroviral Fusion, Uncoating, and Reverse Transcription. The first step in generating the cell-free system involved trapping ASLV-A virions at a stage before the completion of fusion within an intracellular fusion compartment, presumably endosomes (FIG. 16A). This procedure involved binding a subgroup A ASLV vector to human 293 (TVA800) cells expressing glycosylphosphatidylinositol-anchored TVA. Viral entry was then initiated by shifting the cells from 0° C. to 37° C. in the presence of 30 mM NH$_4$Cl, allowing for accumulation of virions within endosomes. The cells were then shifted back to 4° C. in the continued presence of NH$_4$Cl and lysed by using a ball-bearing cell cracker to minimize damage to endosomes (Gorvel et al., 1991; Davey et al., 1985; Gruenberg et al., 1986). A VPNS was then isolated and incubated under conditions that were either permissive (3 mM NH$_4$Cl) or not permissive (63 mM NH$_4$Cl) for virus-cell membrane fusion. ASLV fusion and entry into cells is effectively blocked by 30 mM or higher concentrations of NH$_4$Cl (Mothes et al., 2000; Narayan et al., 2003) but is unaffected by the presence of 3 mM NH$_4$Cl (data not shown).

To assess whether or not viral cores that were released from endosomes were competent for reverse transcription, and to investigate the possible role of cellular factors, the samples were incubated in a buffer that included 3 mM MgCl$_2$, a physiological level (50 µM) of dNTPs, and the supernatant of a 10,000×g spin of a 293 cell extract (293 S10 fraction). A real-time PCR amplification-based assay was then used to quantify the viral DNA products that arose in the cell-free system (FIG. 16A). The oligonucleotide primers used were derived from the U3 and U5 regions of the viral LTR to detect newly synthesized minus-strand DNA products resulting from the first strand-transfer event of reverse transcription (Narayan et al., 2003).

These studies revealed that early reverse transcription products were synthesized in vitro, but only under fusion-permissive conditions (FIG. 16B). Moreover, viral DNA synthesis was absolutely dependent on added $Mg^{2+}$ ions and dNTPs (FIG. 16B). A small number of viral DNA products were observed under fusion nonpermissive conditions in the presence of $Mg^{2+}$ ions and dNTPs (FIG. 16B). These DNA products are probably derived from viral particles released from endosomes, which are broken during preparation of the VPNS.

The maximum amount of viral DNA that was obtained in the cell-free system under fusion-permissive conditions was about 20% of that seen within infected cells (Narayan et al., 2003), demonstrating that the cell-free system is highly efficient.

Cellular Factor(s) Stimulate ASLV Fusion/Uncoating in the Cell-Free System. In the experiment shown in FIG. 16B, cellular factors contained within a 293 S10 fraction were included in the cell-free reaction. To test the contribution of these factors, they were either included or omitted from the cell-free reactions. These studies showed that the 293 S10 fraction increased the initial rate as well as the final extent of viral DNA synthesis in a dose-dependent manner (FIG. 17A). This effect was specific because it was not seen with addition of a similar amount of yeast cell S10 fraction or BSA (FIG. 17B). A preliminary characterization of the 293 S10 factor(s) revealed that they are soluble in nature and are >5 kDa in size (FIG. 17C). Viral DNA synthesis in the cell-free system was also temperature-dependent because it was not observed with samples incubated at 4° C. (FIG. 17A). Taken together, these results indicate that the virus-cell membrane fusion reaction is not sufficient to initiate reverse transcription but instead cellular factors are required.

The 293 Cell Factor(s) Act After Completion of the Low pH-Dependent Step. Consistent with a role for low pH in virus-cell membrane fusion, ASLV-A overcomes the $NH_4Cl$-induced block in infected cells within only 1 minute after inhibitor removal (Narayan et al., 2003). To determine whether virions are trapped at the same stage of infection in the cell-free system, a similar experiment was performed in vitro by releasing the $NH_4Cl$-induced block for different periods of time before restoring the block. These studies showed that virions traversed the $NH_4Cl$-sensitive step in the cell-free system with the same kinetics seen previously with infected cells (FIG. 18A). Therefore, the trapped virus particles used as substrates in the cell-free reaction seem to be blocked at the same stage of entry as those located within intact $NH_4Cl$-treated cells, i.e., at membrane fusion.

To test whether the 293 S10 factor(s) act after the low pH-dependent step, cell-free reactions were performed by first initiating fusion under permissive conditions (3 mM $NH_4Cl$) in the absence of these factors. $NH_4Cl$ was then added to a final concentration of 63 mM to block subsequent rounds of fusion and the 293 S10 fraction was then added to some samples. If the cellular factors were required to stimulate the low pH-dependent step of fusion, then viral DNA should not be synthesized under these conditions. Instead, the cellular factors stimulated viral DNA synthesis (FIG. 18B). Therefore, the 293 cell factor(s) are not required for the low pH-dependent step of viral penetration from endosomes, but instead act at a subsequent step leading to reverse transcription.

ATP Hydrolysis Is Required for Stimulating ASLV and HIV Early DNA Synthesis. To determine whether ATP hydrolysis is required for viral DNA synthesis in the cell-free system, adenosine 5'-[γ-thio]triphosphate, a nonhydrolyzable ATP analogue, was included in some samples. This nucleotide analogue markedly reduced the stimulation of early DNA synthesis in the cell-free system (FIGS. 19A and 21). Furthermore, addition of apyrase to reduce the levels of endogenous ATP present in the 293 S10 fraction resulted in a reduced the amount of ASLV early DNA products (FIG. 19B). Intriguingly, this treatment had little or no effect when apyrase was added 30 minutes or later after initiating the cell-free reaction (FIG. 19B). Together, these data suggest that ATP hydrolysis is required for events leading to the initiation of ASLV and HIV early DNA synthesis.

A Nuclear Extract Promotes ASLV Late DNA Synthesis. Previously, it was shown that most ASLV DNA molecules found in the cytoplasm are incompletely synthesized, and that integration of this DNA does not occur unless reverse transcription is more or less completed (Lee et al., 1991). These observations led to the proposal that nuclear factors may be required for completing reverse transcription of the ASLV genome. This hypothesis was tested directly by adding a nuclear extract to some samples and assessing its effect on early and late DNA production. These experiments revealed that the nuclear extract enhanced late but not early ASLV DNA synthesis (FIG. 20). The level of late viral DNA synthesis in the experiment shown in FIG. 20B was about 4% of that expected from infected cells, i.e., a lower efficiency than that seen previously with early DNA synthesis. Nevertheless, these results indicate that 293 cell nuclear factors may specifically promote ASLV late DNA synthesis and suggest that the cell-free system may be useful for studying steps of retroviral replication after the earliest uncoating events.

HIV-1 Uncoating is Stimulated by 293 Cell Factor(s). To test whether the ASLV-based cell-free system can be employed other viral cores that can be co-assembled with ASLV Env, pseudotyped viruses having HIV-1 cores and EnvA were prepared (Lewis et al., 2001). In control experiments, it was demonstrated that such viruses, designated here as HIV [EnvA], were capable of infecting cells that express GPI-anchored TVA in a low pH-dependent manner, and remain stable when infection was arrested with $NH_4Cl$.

Cell-free reactions were performed with HIV [EnvA]-containing VPNS that was derived from 293 cells expressing GPI-anchored TVA. Synthesis of early HIV-1 DNA products was then monitored using a previously described real-time PCR amplification-based assay to detect minus-strand strong stop DNA, the first product of reverse transcription (Munk et al., 2002). Again, the 293 S10 fraction stimulated viral DNA synthesis, but only under fusion-permissive conditions and only in the presence of added dNTPs (FIG. 22A). Therefore, 293 S10 factor(s) also appear to stimulate HIV-1 DNA synthesis in the cell-free system. Again, these S10 factor(s) were found to be larger than 5 kDa in size (FIG. 22B).

Reconstitution of Cyclosporin A-Inhibition and Lv-1 Restriction of HIV-1 early DNA Synthesis. In contrast to native HIV-1 particles that are believed to fuse at the cell surface under neutral pH conditions after interacting with the CD4 receptor and chemokine co-receptors (Pierson and Doms, 2003), HIV[EnvA] enters cells by a low pH-dependent mechanism following the EnvA-TVA interaction. Since it was possible that this altered pathway of viral entry might change the process of HIV-1 uncoating, factors thought to block this process were tested for inhibition of HIV[EnvA] uncoating in vitro. One of these inhibitors, cyclosporin A can block HIV-1 early DNA synthesis by approximately 75% when it is added to target cells prior to viral challenge (Towers et al., 2003). To determine if this effect was reproduced by the cell-free system, reactions were set up with HIV [EnvA]-containing VPNS either in the presence or absence of 20 µM cyclosporin A. This inhibitor reduced the level of HIV-1 early DNA produced in vitro by approximately 80% (FIG. 23A), i.e. a similar effect to that seen in intact cells (Towers et al., 2003). These findings demonstrate that the cyclosporin A-mediated inhibition of HIV-1 DNA synthesis is reconstituted in the cell-free system.

As a further test of the validity of this system, it was determined whether the phenomenon of Lv-1 restriction of HIV-1 DNA synthesis could be reproduced in vitro. As compared to human cell types, simian CV-1 and FrHL-2 cells demonstrate a 50% and 90% block to HIV-1 DNA synthesis, respectively, and these effects are due to the actions of dominantly-acting Lv-1 restricting factors (Besnier et al., 2002; Cowan et al., 2002; Munk et al., 2002). To determine whether these factors can block HIV-1 DNA synthesis in vitro, HIV [EnvA] fusion and uncoating reactions were performed with a fixed amount of 293 S10 fraction and increasing amounts of either CV-1, FrHL-2, or 293 S10 fractions. The CV-1 and FrHL-2 fractions specifically blocked HIV-1 DNA synthesis in vitro by 50% and by 90%, respectively (FIG. 23B). These effects recapitulate the Lv-1 restriction phenomenon that is seen with these cells, providing a second independent line of evidence that this is a bona fide system for studying early steps of HIV-1 replication.

Discussion

A cell-free system is described that efficiently reconstitutes retroviral membrane fusion, uncoating and reverse transcription in vitro. This system was used to obtain evidence that cytosolic factors and ATP hydrolysis promote the synthesis of ASLV early DNA products, whereas nuclear factors enhance synthesis of late DNA products. These data imply an active, dynamic mechanism for retroviral uncoating involving the recruitment of cellular factors to incoming cores. The cell-free system should now allow for the identification and characterization of these cellular factors.

This cell-free system should allow for an investigation of the molecular events that surround the formation of the viral RTC. Because the system monitors steps that follow immediately after virus-cell membrane fusion leading up to the activation of reverse transcription, it is distinguished from others which have characterized the behavior of viral cores under nonphysiological conditions, e.g., using the endogenous reverse transcription reaction (ERT). The ERT assay involves the artificial disruption of virions with detergents (Goff, 2001; Temin et al., 1972). However, in addition to viral membrane removal, detergent addition affects the integrity of viral cores, raising doubts that the behavior of viral particles in this system reflects that of intracellular viral complexes (Fassati, 1999). Other approaches have been described that monitor the behavior of RTCs that are produced within infected cells before they are isolated and characterized (Fassati, et al., 1999; Fassati et al., 2001). However, these approaches will not detect the uncoating steps that occur immediately after the membrane fusion reaction.

Although the cell-free system is specific and efficient, an about 100-fold increase in ASLV DNA synthesis was observed in intact cells under fusion-permissive conditions (3 mM $NH_4Cl$), as compared to non-fusion-permissive conditions (30 mM $NH_4Cl$) (Narayan et al., 2003). However, in the cell-free system, the level of viral DNA that was obtained under fusion-permissive conditions was only about 7- to 10-fold higher than that seen under non-fusion-permissive conditions (FIGS. 16 and 17). Presumably, this effect is caused by the release of ASLV cores during the mechanical cell lysis of infected cells, where some endosomal/viral membranes may be ruptured. Consistent with this hypothesis, a higher level of viral DNA was synthesized under fusion non-permissive conditions when the level of dNTPs was increased to a nonphysiological concentration (i.e., 500 µM). Presumably, the particles that are released from ruptured endosomes are unable to efficiently synthesize DNA in the presence of physiological dNTP levels.

A small level of viral DNA was produced in the cell-free system under fusion-permissive conditions in the absence of any added 293 cellular factors (FIGS. 17A and 18B). This effect is probably caused by the carryover of cellular factors contained in the VPNS, which is diluted 10-fold into the in vitro reaction.

The cellular factor(s) that stimulated ASLV early DNA synthesis acted after the low pH-dependent step of viral entry (membrane fusion) was completed. This suggests that the retroviral core may recruit cellular factors and dNTPs to stimulate uncoating events involved in initiating reverse transcription. Therefore, retroviral uncoating may not simply be a passive disassembly process, but rather it may be an active, dynamic process. Furthermore, the nuclear factor enhancement of ASLV late DNA synthesis suggests that uncoating and reverse transcription may occur via discrete intermediates involving different cellular factors as the RTC progresses to form the preintegration complex. Indeed, the notion that cellular factors are involved in these postfusion steps is consistent with previous observations that incoming retroviral particles associate with components of the host cell cytoplasm. For example, HIV-1 cores have been reported to associate with the host cell cytoskeleton, including actin and microtubules (McDonald et al., 2002; Bukrinskaya et al., 1998). Also, partial purification of subviral complexes from cells suggest that retroviral cores may undergo changes in composition during entry (Fassati et al., 1999; Fassati et al., 2001). It is now imperative to monitor the biochemical changes in RTCs formed in the cell-free system and relate these changes to those observed within intact cells during an actual infection. The cell-free system may also prove useful in identifying the potential biochemical and structural intermediates in retroviral uncoating through the analysis of virions that contain mutant ASLV or HIV-1 capsid proteins, which are arrested at an early step of replication before reverse transcription (Cairns et al., 2001).

In the cell-free system, ATP hydrolysis was required during the first 30 minutes after membrane fusion. However, it remains to be determined exactly how cellular factors and ATP hydrolysis may function to trigger, and perhaps orchestrate, the earliest steps of retroviral uncoating. One possibility is that ATP is used as a substrate to phosphorylate viral proteins. Indeed, for HIV-1, phosphorylation of serine residues in the viral matrix and capsid proteins has been implicated in these early events (Cartier et al., 1999; Kaushik et al., 2004). A second possibility is that ATP is required for the function of a molecular chaperone that may play a role in viral uncoating. In support of this idea, it has been reported that HIV-1 particles contain substantial amounts of certain members of the Hsp70 family of ATPases (Gurer et al., 2002). With the cell-free system now in hand, it should be possible to distinguish between these and other possible roles for ATP in viral uncoating.

HIV-1 normally enters cells by fusion at the plasma membrane after binding the CD4 receptor and chemokine co-receptors (Pierson and Doms, 2003). Although the HIV [EnvA] particles instead fuse with cellular membranes at low pH in the cell-free system, there are two independent lines of evidence which suggest that the uncoating of these particles follows the normal requirements for HIV-1. Specifically, HIV-1 DNA synthesis in vitro was inhibited by cyclosporin A and was subject to Lv-1 restriction, as observed in intact cells challenged with wild-type HIV-1 (Bieniasz, 2003; Towers et al., 2003).

Early postfusion events remain largely unexplored for most enveloped viruses (Whittaker et al., 2000). In principle, it should be possible to apply the ASLV-based cell-free system to study the uncoating mechanism of any viral core that can be coassembled with ASLV Env. Indeed, HIV-1 uncoating has been observed with pseudotyped (mixed) HIV-1 [ASLV-A Env] particles. Thus, using these and other pseudotyped particles in the cell-free system, it should be possible to reconstitute uncoating events of a number of other viruses. In the case of HIV-1, this would be particularly important because uncoating remains a thus far unexplored target for therapeutics in the viral life cycle.

REFERENCES

Adkins et al., *J. Virol.*, 74:3572 (2000).
Aiken, *J. Virol.*, 71:5871C (1997).
Anderson, *Annu. Rev. Biochem.*, 67:199 (1998).
Ausubel et al., *Current Protocols in Molecular Biology*, Wiley, NY, Vol. 1 (2000).
Baker et al., *Mol. Cell*, 3:309 (1999).
Barnard et al., *Curr. Top. Immunol. Microbiol.*, 281:107 (2003).
Bates et al., *Cell*, 74:1043 (1993).
Benmerah et al., *J. Cell Sci.*, 112:1303 (1999).
Besnier et al., *Proc. Natl. Acad. Sci. USA*, 99:11920 (2002).
Bieniasz et al., *Trends Microbiol.*, 11:286 (2003).
Bieniasz, *Nat. Immunol.*, 5:1109 (2004).
Boerger et al., *Proc. Natl. Acad. Sci. USA*, 96:9867 (1999).
Bowerman et al., *Genes Dev.*, 3:469 (1989).
Braaten et al., *J. Virol.*, 70:3551 (1996).
Bradley, The use of somatic cell genetics to identify cellular factors involved in host-pathogen interactions, Harvard University, Cambridge (2002).
Brodsky et al., *Annu. Rev. Cell Dev. Biol.*, 17:517 (2001).
Brojatsch et al., *Cell*, 87:845 (1996).
Brown et al., *Annu. Rev. Cell Dev. Biol.*, 14:111 (1998).
Brown et al., *Cell*, 49:347 (1987).
Bui et al., *J. Virol.*, 70:8391 (1996).
Bukrinskaya et al., *J. Exp. Med.*, 188:2113 (1998).
Bukrinsky et al., *Proc. Natl. Acad. Sci. USA*, 89:6580 (1992).
Bukrinsky et al., *Proc. Natl. Acad. Sci. USA*, 90:6125 (1993).
Bullough et al., *Nature*, 371:37 (1994).
Cairns et al., *J. Virol.*, 75:242 (2001).
Carr et al., *Proc. Natl. Acad. Sci USA*, 94:14306 (1997).
Cartier et al., *J. Biol. Chem.*, 274:19434 (1999).
Chamberlain, *Proc. Natl. Acad. Sci. USA*, 98:5619 (2001).
Chan et al., *Cell*, 106:117 (2001).
Chan et al., *Cell*, 89:263 (1997).
Chatterjee et al., *EMBO J.*, 20:1583 (2001).
Chazal et al., *J. Virol.*, 75:4014 (2001).
Chazal et al., *Microbiol. Mol. Biol. Rev.*, 67:226 (2003).
Chen et al., *Cell*, 97:165 (1999).
Chen et al., *Proc. Natl. Acad. Sci. USA*, 96:8967 (1999a).
Coffin et al., Retroviruses (Cold Spring Harbor, Cold Spring Harbor Laboratory Press) (1997).
Conner et al., *Nature*, 422:37 (2003).
Connolly et al., *J. Virol.*, 68:2760 (1994).
Cowan et al., *Proc. Natl. Acad. Sci. USA*, 99:11914 (2002).
Damke et al., *J. Cell Biol.*, 127:915 (1994).
Davey et al., *Cell*, 43:643 (1985).).
DeTulleo et al., *Embo J.*, 17:4585 (1998).
Diaz-Griffero et al., *J. Virol.*, 76:12866 (2002).
Dvorin et al., In: *Current Topics in Microbiology and Immunology*, J. A. T. Young, ed. (Berlin, Springer), pp. 179-208 (2003).
Earp et al., *J. Virol.*, 77:3058 (2003).
Eckert et al., *Annu. Rev. Biochem.*, 70:777 (2001).
Empig et al., *J. Virol.*, 76:5266 (2002).
Farnet et al., *J. Virol.*, 65:1910 (1991).
Farrell et al., *J. Virol.*, 76:6762 (2002).
Fassati et al., *J. Virol.*, 73:8919 (1999).
Fassati et al., *J. Virol.*, 75:3626 (2001).
Forshey et al., *J. Virol.*, 76:5667 (2002).
Fra et al., *J. Biol. Chem.*, 269:30745 (1994).
Franke et al., *Nature*, 372:359 (1994).
Freed et al., *J. Virol.*, 70:341 (1996).
Gamble et al., *Cell*, 87:1285 (1996).
Gao et al., *Mol. Biol. Cell.*, 10:1705 (1999).
Gilbert et al., *J. Virol.*, 68:5623 (1994).
Gilbert et al., *J. Virol.*, 64:5106 (1990).
Goff, *J. Gene Med.*, 3:517 (2001).
Gorrel et al., *Cell*, 64:915 (1991).
Gruenberg et al., *Ann. Rev. Cell Biol.*, 5:453 (1989).
Gruenberg et al., *EMBO J.*, 5:3091 (1986).
Gruenberg, *Nat. Rev. Mol. Cell. Biol.*, 2:721 (2001).
Gurer et al., *J. Virol.*, 76:4666 (2002).
Hatziioannou et al., *Embo J.*, 22:385 (2003).
Helenius, *Cell*, 69:577 (1992).
Ikonen, *Curr. Opin. Cell Biol.*, 13:470 (2001).
Joki-Korpela et al., *J. Virol.*, 75:1958 (2001).
Karageorgos, et al., *AIDS Res. Hum. Retroviruses*, 9:817 (1993).
Karpas et al., *PNAS*, 89:835 (1992).
Kaushik et al., *J. Virol.*, 78:2319 (2004).
Kaykas, *EMBO J.*, 20:2641 (2001).
Kirchhausen, *Annu. Rev. Cell Dev. Biol.*, 15:705 (1999).
Kizhatil et al., *J. Virol.*, 71:7145 (1997).
Knauss et al., *J. Virol.*, 76:5404 (2002).
Kootstra et al., *Proc. Natl. Acad. Sci. USA*, 100:1298 (2003).
Kurzchalia et al., *Curr. Opin. Cell. Biol.*, 11:424 (1999).
Lamaze et al., *Mol. Cell*, 7:661 (2001).
Lee et al., *Mol. Cell. Biol.*, 11:1419 (1991).
Lewis et al., *J. Virol.*, 75:9339 (2001).
Li et al., *Embo J.*, 20:3272 (2001).
Liao et al., *AIDS Res. Hum. Retrovir.*, 17:1009 (2001).
Lu et al., *J. Virol.*, 76:6701 (2002).
Lu et al., *Virology*, 276:251 (2000).
Luban et al., *Cell*, 73:1067 (1993).
Luban, *Cell*, 87:1157 (1996).
Malashkevich et al., *Proc. Natl. Acad. Sci. USA*, 96:2662 (1999).
Mallard et al., *J. Cell Biol.*, 143:973 (1998).
Manes et al., *EMBO Rep.*, 1:190 (2000).
Marsh et al., *Adv. Virus Res.*, 36:107 (1989).
Martin et al., *Cell*, 67:117 (1991a).
Martin et al., *J. Virol.*, 65:232 (1991b).
Matlin et al., *J. Mol. Biol.*, 156:609 (1982).
Mayor et al., *EMBO J.*, 17:4626 (1998).

McDonald et al., *J. Cell. Biol.*, 159:441 (2002).
Melikyan et al., *J. Cell. Biol.*, 151:413 (2000).
Melikyan et al., *J. Virol.*, 78:3753 (2004).
Miller et al., *J. Virol.*, 71:5382 (1997).
Mothes et al., *Cell*, 103:679 (2000).
Mousavi et al., *Biochem. J. Pt.*, (2003).
Mukherjee et al., *Physiol. Rev.*, 77:759 (1997).
Munk et al., *Proc. Natl. Acad. Sci. USA*, 99:13843 (2002).
Nichols et al., *J. Cell Biol.*, 153:529 (2001).
Nichols et al., *Trends Cell. Biol.*, 11:406 (2001).
Ohkuma et al., *J. Cell Biol.*, 90:656 (1981).
Ohkuma et al., *Proc. Natl. Acad. Sci. USA*, 75:3327 (1978).
Orlandi et al., *J. Cell Biol.*, 141:905 (1998).
Ory et al., *Proc. Natl. Acad. Sci. USA*, 93:11400 (1996).
Pelkmans et al., *Curr. Opin. Cell Biol.*, 15:414 (2003).
Pelkmans et al., *Nat. Cell Biol.*, 3:473 (2001).
Pelkmans et al., *Science*, 296:535 (2002).
Pho et al., *J. Virol.*, 74:2288 (2000).
Pierson et al., In: *Current Topics in Microbiology and Immunology*, J. A. T. Young, ed. (Berlin, Springer), pp. 1-28 (2003)
Pinto et al., *Cell*, 69:517 (1992).
Popik et al., *J. Virol.*, 76:4709 (2002).
Rai et al., *Proc. Natl. Acad. Sci. USA*, 98:4443 (2001).
Robinson et al., In: *Cell Biology: A Laboratory Handbook*, Celis (ed.), Academic, NY, vol. 2, pp, 248-257 (1995).
Sabharanjak et al., *Dev. Cell*, 2:411 (2002)
Saphire et al., *J. Virol.*, 76:2255 (2002).
Schafer, *Curr. Opin. Cell. Biol.*, 14:76 (2002).
Schwartz et al., *Mol. Cell* 9:505 (2002).
Sharma et al., *Semin. Cell Dev. Biol.*, 13:205 (2002).
Sheehy et al., *Nature*, 418:646 (2002).
Sieczkarski et al., *J. Virol.*, 76:10455 (2002).
Simon et al., *J. Virol.*, 70:5297 (1996).
Simons et al., *Nat. Rev. Mol. Cell. Biol.*, 1:31 (2000).
Simons et al., *Nature*, 387:569 (1997).
Skehel et al., *Annu. Rev. Biochem.*, 69:531 (2000).
Smith et al., *J. Virol.*, 72:3501 (1998).
Smith et al., *J. Virol.*, 78:1403 (2004).
Snitkovsky et al., *J. Virol.*, 74:9540 (2000).
Snitkovsky et al., *J. Virol.*, 75:1571 (2001).
Snitkovsky et al., *Proc. Natl. Acad. Sci. USA*, 95:7063 (1998).
Snyers et al., *J. Virol.*, 77:5360 (2003).
Stremlau et al., *Nature*, 427:848 (2004).
Taplitz et al., *J. Virol.*, 71:7814 (1997)
Temin et al., *Adv. Virus Res.*, 17:129 (1972).
Thali et al., *Nature*, 372:363 (1994).
Towers et al., *AIDS Dev.*, 5:156 (2003).
Towers et al., *Nat. Med.*, 9:1138 (2003).
von Schwedler et al., *J. Virol.*, 67:4945 (1993).
Wang et al., *J. Virol.*, 76:2848 (2002).
Weiss, In The Retroviridae, J. A. Levy, ed. (New York, Plenum Press), pp. 1-108 (1993).
Weissenhorn et al., *Mol. Cell*, 2:605 (1998).
Weissenhorn et al., *Nature*, 387:426 (1997).
Whittaker et al., *Annu. Rev. Cell Dev. Biol.*, 16:627 (2000).
Young et al., *J. Virol.*, 67:1811 (1993).
Young, Virus Entry and Uncoating. In Fundamental Virology, D. M. Knipe, and P. M. Howley, eds. (Philadelphia, Lipppincott Williams & Wilkins), pp. 87-105 (2001).
Yu et al., *J. Virol.*, 66:4966 (1992).
Zingler et al., *J. Virol.*, 70:7510 (1996).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A cell-free method for release of viral cores of enveloped viruses from endosomes, comprising:
   a) providing a cell-free sample comprising intact endosomes comprising fusion arrested enveloped viral particles, which endosomes are isolated from cells that express one or more viral receptors including the viral receptor TVA and are infected with a pseudotyped enveloped virus having a subgroup A ASLV envelope protein, wherein the endosomes are isolated in the presence of an amount of a lysosomotropic agent that elevates endosomal pH effective to arrest membrane fusion; and
   b) subjecting the sample to conditions that allow for virus particle-endosomal membrane fusion and release of viral cores from endosomes, yielding a composition.

2. The method of claim 1 further comprising detecting or determining viral uncoating or viral nucleic acid replication in the composition.

3. The method of claim 1 wherein the pseudotyped virus comprises rhabdovirus, orthomyxovirus, paramyxovirus, retrovirus, lentivirus, bunyavirus, arenavirus, hepadnavirus, flavivirus, coronavirus, or filovirus cores.

4. The method of claim 1 wherein the virus is a retrovirus or lentivirus.

5. The method of claim 1 wherein the cells are recombinant cells.

6. The method of claim 1 wherein the cells are mammalian cells.

7. The method of claim 1 or 2 further comprising contacting the sample with one or more agents and detecting or determining whether the one or more agents alter post-fusion viral uncoating or nucleic acid replication.

8. The method of claim 1 wherein prior to isolating endosomes the cells are contacted with one or more agents.

9. The method of claim 8 further comprising detecting or determining whether the one or more agents alter post-fusion viral uncoating or nucleic acid replication.

10. The method of claim 7 wherein the one or more agents inhibit or block viral uncoating.

11. The method of claim 7 wherein the viral core is a HIV core and wherein the one or more agents inhibit or block HIV-1 uncoating.

12. The method of claim 2 further comprising identifying one or more cellular factors that modulate post-fusion viral uncoating or nucleic acid replication.

13. The method of claim 1 further comprising identifying one or more cellular factors that alter Lv-1 restriction.

14. The method of claim 2 further comprising contacting the composition with one or more agents and detecting or determining whether the one or more agents alter viral uncoating or nucleic acid replication.

15. The method of claim 1 wherein about 70% of the endosomes in the sample are intact.

16. A method to prepare a cell-free sample comprising isolated endosomes having fusion arrested enveloped viral particles, comprising:
   a) infecting cells that express one or more viral receptors including the viral receptor TVA with a pseudotyped enveloped virus having a subgroup A ASLV envelope protein in the presence of an amount of a lysosomotropic agent that elevates endosomal pH effective to arrest membrane fusion; and
   b) isolating endosomes from the infected cells.

* * * * *

UNITED STATES PATENT AND TRADEMARK OFFICE
CERTIFICATE OF CORRECTION

PATENT NO.      : 7,598,072 B2
APPLICATION NO. : 11/007145
DATED           : October 6, 2009
INVENTOR(S)     : Young et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 267 days.

Signed and Sealed this

Twenty-eighth Day of September, 2010

David J. Kappos
*Director of the United States Patent and Trademark Office*

SEQUENCE LISTING

<160> NUMBER OF SEQ ID NOS: 3

<210> SEQ ID NO 1
<211> LENGTH: 20
<212> TYPE: DNA
<213> ORGANISM: Avian sarcoma and leukosis virus (ASLV)

<400> SEQUENCE: 1
accactgaat tccgcattgc                                         20

<210> SEQ ID NO 2
<211> LENGTH: 21
<212> TYPE: DNA
<213> ORGANISM: Avian sarcoma and leukosis virus (ASLV)

<400> SEQUENCE: 2
ggccgaccac tattccctaa c                                       21

<210> SEQ ID NO 3
<211> LENGTH: 25
<212> TYPE: DNA
<213> ORGANISM: Avian sarcoma and leukosis virus (ASLV)

<400> SEQUENCE: 3
ccctgacgac tacgagcacc tgcat                                   25